US012697064B2

(12) United States Patent
Webster et al.

(10) Patent No.: US 12,697,064 B2
(45) Date of Patent: Aug. 4, 2026

(54) SURVEY-BASED VARIABLE USER INTERFACE AND PATIENT ENGAGEMENT FEATURES FOR MOBILE COMMUNICATION DEVICE INCLUDED IN WEARABLE MEDICAL DEVICE SYSTEM

(71) Applicant: WEST AFFUM HOLDINGS DAC, Dublin (IE)

(72) Inventors: Brian D. Webster, Mercer Island, WA (US); Catherine Smith, Wellesley, MA (US); Amy E. Blatt, Walnut Creek, CA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 200 days.

(21) Appl. No.: 18/771,731

(22) Filed: Jul. 12, 2024

(65) Prior Publication Data

US 2025/0017529 A1     Jan. 16, 2025

Related U.S. Application Data

(60) Provisional application No. 63/526,297, filed on Jul. 12, 2023.

(51) Int. Cl.
*A61B 5/00* (2006.01)
*G16H 10/20* (2018.01)

(52) U.S. Cl.
CPC .......... *A61B 5/6802* (2013.01); *A61B 5/0002* (2013.01); *A61B 5/7435* (2013.01); *G16H 10/20* (2018.01)

(58) Field of Classification Search
CPC ... A61B 5/6802; A61B 5/0002; A61B 5/7435; A61B 5/0022; A61B 5/0205;
(Continued)

(56) References Cited

U.S. PATENT DOCUMENTS 3,724,355 A     4/1973   Busch et al.
3,724,455 A     4/1973   Unger
(Continued)

FOREIGN PATENT DOCUMENTS

DE     102005060985 A1     6/2007
EP         2305110 A1     4/2011
(Continued)

OTHER PUBLICATIONS

HeartStart MRx and Xl Aed Algorithm—Application Note, Jul. 2011, Edition 2 Philips Healthcare, USA.
(Continued)

*Primary Examiner* — An T Nguyen
(74) *Attorney, Agent, or Firm* — Seed Intellectual Property Law Group LLP

(57)                    ABSTRACT

A medical system includes a wearable medical device configured to be worn by a patient, remote server(s), and a mobile device. The mobile device includes at least one processor and a display, the at least one processor being configured to establish communication between the mobile device, the wearable medical device, and the remote server(s) when the mobile device is powered on and within a predetermined range of the wearable medical device. The at least one processor is further configured to provide an interactive survey on the display to receive one or more user inputs, update a graphical user interface on the display based on the one or more user inputs, and cause one or more patient engagement features to be displayed on the display. Upon establishing communication between the mobile device, the wearable medical device, and the remote server(s), patient data is transmitted to the remote server(s).

20 Claims, 13 Drawing Sheets

(58) Field of Classification Search
CPC ........ A61B 5/021; G16H 10/20; G16H 20/30; G16H 40/63; G16H 40/67

See application file for complete search history.

(56) References Cited

U.S. PATENT DOCUMENTS

| | | | |
|---|---|---|---|
| 4,583,524 A | 4/1986 | Hutchins | |
| 4,619,265 A | 10/1986 | Morgan et al. | |
| 4,666,432 A | 5/1987 | McNeish et al. | |
| 4,698,848 A | 10/1987 | Buckley | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,429,593 A | 7/1995 | Matory | |
| 5,474,574 A | 12/1995 | Payne et al. | |
| 5,618,208 A | 4/1997 | Crouse et al. | |
| 5,662,690 A | 9/1997 | Cole et al. | |
| 5,708,978 A | 1/1998 | Johnsrud | |
| 5,741,306 A | 4/1998 | Glegyak et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,280,461 B1 | 8/2001 | Glegyak et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,437,083 B1 | 8/2002 | Brack et al. | |
| 6,450,942 B1 | 9/2002 | Lapanashvili et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,099,715 B2 | 8/2006 | Korzinov et al. | |
| 7,212,850 B2 | 5/2007 | Prystowsky et al. | |
| 7,559,902 B2 | 7/2009 | Ting et al. | |
| 7,587,237 B2 | 9/2009 | Korzinov et al. | |
| 7,753,759 B2 | 7/2010 | Pintor et al. | |
| 7,865,238 B2 | 1/2011 | Brink | |
| 7,870,761 B2 | 1/2011 | Valentine et al. | |
| 7,907,996 B2 | 3/2011 | Prystowsky et al. | |
| 7,941,207 B2 | 5/2011 | Korzinov | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,527,028 B2 | 9/2013 | Kurzweil et al. | |
| 8,548,557 B2 | 10/2013 | Garstka et al. | |
| 8,560,044 B2 | 10/2013 | Kurzweil et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,706,255 B2 | 4/2014 | Phillips et al. | |
| 8,742,349 B2 | 6/2014 | Urbon et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,084,583 B2 | 7/2015 | Mazar et al. | |
| 9,089,685 B2 | 7/2015 | Sullivan et al. | |
| 9,119,547 B2 | 9/2015 | Cazares et al. | |
| 9,131,901 B2 | 9/2015 | Volpe et al. | |
| 9,132,267 B2 | 9/2015 | Kaib | |
| 9,265,432 B2 | 2/2016 | Warren et al. | |
| 9,345,898 B2 | 5/2016 | Piha et al. | |
| 9,408,548 B2 | 8/2016 | Volpe et al. | |
| 9,445,719 B2 | 9/2016 | Libbus et al. | |
| 9,454,219 B2 | 9/2016 | Volpe et al. | |
| 9,579,020 B2 | 2/2017 | Libbus et al. | |
| 9,592,403 B2 | 3/2017 | Sullivan | |
| 9,598,799 B2 | 3/2017 | Shoshani et al. | |
| 9,675,804 B2 | 6/2017 | Whiting et al. | |
| 9,724,008 B2 | 8/2017 | Sullivan et al. | |
| 9,878,171 B2 | 1/2018 | Kaib | |
| 9,895,105 B2 | 2/2018 | Romem | |
| 9,901,741 B2 | 2/2018 | Chapman et al. | |
| RE46,926 E | 7/2018 | Bly et al. | |
| 10,016,613 B2 | 7/2018 | Kavounas | |
| 10,076,656 B2 | 9/2018 | Dar et al. | |
| 10,192,387 B2 | 1/2019 | Brinig et al. | |
| 10,307,133 B2 | 6/2019 | Kaib | |
| 10,463,867 B2 | 11/2019 | Kaib et al. | |
| 10,589,110 B2 | 3/2020 | Oskin et al. | |
| 10,599,814 B2 | 3/2020 | Landrum et al. | |
| 2002/0181680 A1 | 12/2002 | Linder et al. | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0161554 A1 | 6/2015 | Sweeney et al. | |
| 2015/0297135 A1 | 10/2015 | Shoshani et al. | |
| 2015/0328472 A1 | 11/2015 | Sullivan et al. | |
| 2016/0004831 A1 | 1/2016 | Carlson et al. | |
| 2016/0076175 A1 | 3/2016 | Rock et al. | |
| 2016/0076176 A1 | 3/2016 | Rock et al. | |
| 2016/0082277 A1 | 3/2016 | Foshee, Jr. et al. | |
| 2016/0113581 A1 | 4/2016 | Amir et al. | |
| 2016/0256104 A1 | 9/2016 | Romem et al. | |
| 2016/0283900 A1 | 9/2016 | Johnson et al. | |
| 2017/0014073 A1 | 1/2017 | Shoshani et al. | |
| 2017/0027469 A1 | 2/2017 | Amir et al. | |
| 2017/0036066 A1 | 2/2017 | Chahine | |
| 2017/0040758 A1 | 2/2017 | Amir et al. | |
| 2017/0162840 A1 | 6/2017 | Pendry | |

(56) References Cited

U.S. PATENT DOCUMENTS

| | | | |
|---|---|---|---|
| 2017/0319862 A1 | 11/2017 | Foshee, Jr. et al. | |
| 2017/0367591 A1 | 12/2017 | Jorgensen | |
| 2018/0116537 A1 | 5/2018 | Sullivan et al. | |
| 2018/0117299 A1 | 5/2018 | Gustavson et al. | |
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0321650 A1 | 10/2019 | Raymond et al. | |
| 2022/0105288 A1* | 4/2022 | Beck | A61B 5/746 |
| 2024/0148310 A1* | 5/2024 | Sharvit | A61B 5/361 |
| 2024/0282420 A1* | 8/2024 | Boschee | A61N 1/046 |

FOREIGN PATENT DOCUMENTS

| | | | |
|---|---|---|---|
| JP | 4320257 B2 | 8/2009 | |
| JP | 2014526282 A | 10/2014 | |
| JP | 5963767 B2 | 8/2016 | |
| WO | 98/39061 A2 | 9/1998 | |
| WO | 2011/146448 A1 | 11/2011 | |
| WO | 2012/064604 A1 | 5/2012 | |
| WO | 2012/151160 A1 | 11/2012 | |
| WO | 2015/056262 A1 | 4/2015 | |

OTHER PUBLICATIONS

Helmut U. Klein et al., "Risk Stratification for Implantable Cardioverter Defibrillator Therapy: The Role of the Wearable Cardioverter-Defibrillator, Clinical update," European Heart Journal, European Society of Cardiology, May 31, 2013, pp. 1-14.

Lifecor "LifeVest System Model WCD 3100 Operator's Manual", 2006, PN 20B0040 Rev FI, Zoll Lifecor Corporation, Pittsburgh, PA.

"LifeVest Model 4000 Patient Manual", Zoll, 2009, PN 20B0047 Rev B.

Pagan-Carlo et al., "Encircling Overlapping Multipulse Shock Waveforms for Transthoracic Defibrillation," JACC Journals, Dec. 1998, vol. 32, Issue 7, pp. 2065-2071.

"The LifeVest Network/Patient Data Management System", Zoll, 2015, 20C0498 Rev A.

Zoll, LifeVest, Proven protection from Sudden Cardiac Death, 2017, Pittsburgh PA, USA, 4 pages.

International Search Report and Written Opinion for PCT Application No. PCT/US2015/051726, dated May 20, 2016, European Patent Office, Rijswijk, (11 pages).

* cited by examiner

500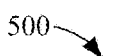

Select a language: <u>502</u>

English

Español

中文

More Languages...

On a scale from 1 to 5, how detailed would you like your instructions to be?

<u>504</u>

| 1 | 2 | 3 | 4 | 5 |

Which statement best represents your past experience with smartphones?
<u>506</u>

I have never used a smartphone before.

I have used a smartphone before but would not say I'm experienced with them.

I am somewhat comfortable using a smartphone.

I am very comfortable using a smartphone.

<u>508</u>

Select a button Size:

| 1 | 2 | 3 | 4 | 5 |

Which font size would you like for your mobile communication device?
<u>510</u>

Aa   Aa   Aa   Aa   Aa

Which background color would you like for your mobile communication device?
<u>512</u> yellow   green   blue   orange   purple

| WCD Wear Time in % or x̄ of hrs/day* | Compliance Status Tier |
|---|---|
| 93% \| 22.5 hrs/day | Platinum |
| 83% \| 20 hrs/day | Gold |
| 75% \| 18 hrs/day | Silver |
| 63% \| 15 hrs/day | Bronze |
| 50% \| 12 hrs/day | Red |

800

802

900

1000

18m ago
Great work today! You wore your WCD for 23/24 hours. Your commitment to wearing your WCD is an important part of your recovery as you are protected when properly wearing your ASSURE System and the heart rhythm data being collected helps your doctor identify important information about your health.

—1002

Yesterday, 3:22 PM
John, yesterday you only wore your WCD for 11/24 hours. Please remember to wear your WCD at all times except for showering, bathing, or swimming. If you need assistance or have questions, please contact the ASSURE Helpline at (XXX) XXX-XXXX.

—1004

now
Nice work! You achieved a 7-day streak of wearing your WCD for 22.5 hours per day or more. You are in the top 10% of patients on our national patient leaderboard!
Keep it up!

—1006

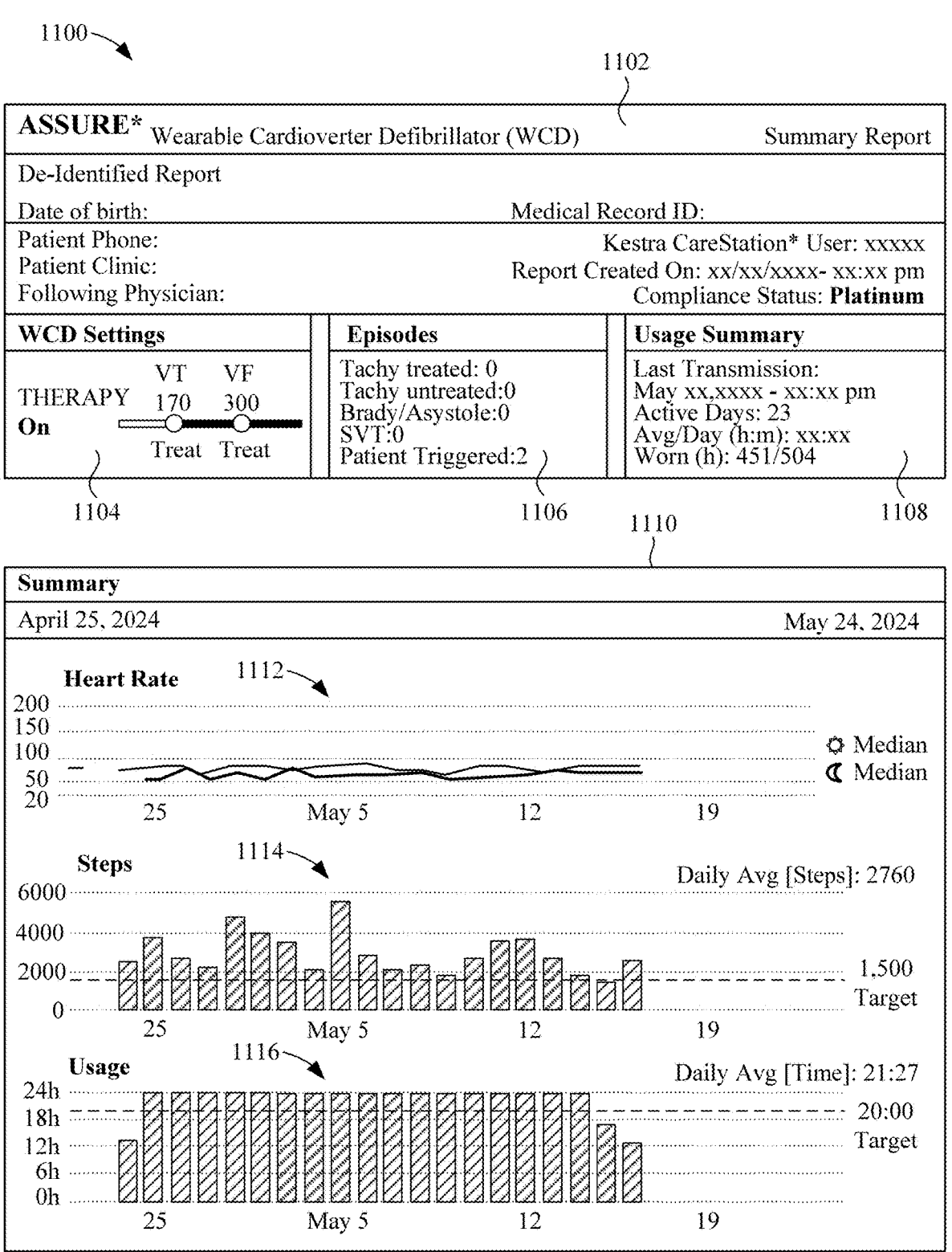

ASSURE* Wearable Cardioverter Defibrillator (WCD)    Summary Report

De-Identified Report

Date of birth:    Medical Record ID:

Patient Phone:    Kestra CareStation* User: xxxxx
Patient Clinic:    Report Created On: xx/xx/xxxx- xx:xx pm
Following Physician:    Compliance Status: Platinum

| WCD Settings | Episodes | Usage Summary |
|---|---|---|
| THERAPY On    VT 170    VF 300    Treat  Treat | Tachy treated: 0  Tachy untreated:0  Brady/Asystole:0  SVT:0  Patient Triggered:2 | Last Transmission:  May xx,xxxx - xx:xx pm  Active Days: 23  Avg/Day (h:m): xx:xx  Worn (h): 451/504 |

1104    1106    1110    1108

Summary

April 25, 2024    May 24, 2024

Heart Rate    1112

200
150
100
50
20
    25    May 5    12    19

☼ Median
☾ Median

Steps    1114    Daily Avg [Steps]: 2760

6000
4000
2000
0
    25    May 5    12    19

1,500 Target

Usage    1116    Daily Avg [Time]: 21:27

24h
18h
12h
6h
0h
    25    May 5    12    19

20:00 Target

FIG. 11

SURVEY-BASED VARIABLE USER INTERFACE AND PATIENT ENGAGEMENT FEATURES FOR MOBILE COMMUNICATION DEVICE INCLUDED IN WEARABLE MEDICAL DEVICE SYSTEM

CROSS-REFERENCE TO RELATED APPLICATIONS

This application claims priority to and the benefit of the provisional patent application No. 63/526,297 titled "SURVEY-BASED VARIABLE USER INTERFACE AND PATIENT ENGAGEMENT FEATURES FOR MOBILE COMMUNICATION DEVICE INCLUDED IN WEARABLE MEDICAL DEVICE SYSTEM", filed in the United States Patent and Trademark Office on Jul. 12, 2023. The specification of the above referenced patent application is incorporated herein by reference in its entirety.

TECHNICAL FIELD

The present technology relates to a wearable medical system that transmits patient's data to one or more remote servers and more particularly, but not by way of limiting, the present technology relates to provision of a survey-based variable user interface and engagement features for a mobile communication device to encourage pairing thereto to a wearable medical device.

BACKGROUND

Wearable medical systems typically include a mobile communication device for relaying patient data from a wearable medical device to a remote server. The patient data is useful in tracking the effectiveness of the wearable medical device as the wearable medical device is ideally worn by a patient for long durations such as at least 23 hours per day. However, not all patients using such wearable medical systems choose to use the mobile communication device for a variety of reasons. For example, due to the older age demographic of patients, some patients are unfamiliar or uncomfortable using mobile communication devices, which may lead to such patients avoiding the mobile communication devices altogether. Generally, the patients interact with the mobile communication device via a user interface. In certain scenarios, user interfaces may be complex or not user-friendly. Thus, there are high chances that the patients are unable to use or comprehend elements of the user interface and feel discomfort during the interaction with the mobile communication device, leading to poor patient engagement.

As another example, some patients experience varying degrees of memory loss, which is another contributing factor to the lack of mobile communication device usage or pairing. As yet another example, the mobile communication device may become out of range due to mobility of the patient or the patient may fail to keep the mobile communication device consistently charged. In either scenario, the mobile communication device may be left unpaired and may not be able to effectively transmit the patient data to the remote server.

SUMMARY

The present disclosure relates to a medical system for transmitting patient data between a wearable medical device worn by a patient and one or more remote servers. In one aspect of the present disclosure, the medical system includes the wearable medical device, one or more remote servers, and a mobile device. The wearable medical device includes a patient data storage module operable to store patient data. The mobile device includes at least one processor and a display, and is configured to establish communication between the wearable medical device and the one or more remote servers. The at least one processor is configured to establish communication between the mobile device, the wearable medical device, and the one or more remote servers when the mobile device is powered on and within a predetermined range of the wearable medical device. The at least one processor is further configured to provide an interactive survey on the display to receive one or more user inputs and update a graphical user interface on the display based on the one or more user inputs. Furthermore, the at least one processor is configured to cause one or more patient engagement features to be displayed on the display, the one or more patient engagement features configured to increase patient engagement with the mobile device, thereby increasing a duration of established communication between the mobile device, the wearable medical device, and the one or more remote servers. When communication is established between the mobile device, the wearable medical device, and the one or more remote servers, the patient data is transmitted to the one or more remote servers from the patient data storage module.

The present disclosure further relates to the interactive survey that may include one or more visual interface selections including one or more of a language selection, a mobile device usage level selection, a level of instruction detail selection, a button size selection, a font size selection, and a background color selection. The interactive survey may further include one or more audio interface selections. The one or more patient engagement features include interactive games, notifications, programmable timed messages, photos, music, podcasts, and news stories. The at least one processor is further configured to automatically update one or more settings to increase communication between the wearable medical device, the mobile device, and the one or more remote servers when an interaction threshold is exceeded.

The present disclosure also relates to the one or more remote servers that are configured to analyze patient data and provide patient data to medical service providers. The wearable medical device further includes a connection verification module which is configured to provide an alert when the wearable medical device is being worn by the patient and communication has not been established between the wearable medical device, the mobile device, and the one or more remote servers for a disconnection duration. The alert is an audible alert or visual alert provided on the wearable medical device. When communication between the mobile device, the wearable medical device, and the one or more one or more remote servers is not established, no patient data is transmitted from the wearable medical device to the one or more remote servers.

BRIEF DESCRIPTION OF THE DRAWINGS

The above-mentioned implementations are further described herein with reference to the accompanying figures. It should be noted that the description and figures relate to exemplary implementations and should not be construed as a limitation to the present disclosure. It is also to be understood that various arrangements may be devised that, although not explicitly described or shown herein, embody the principles of the present disclosure. Moreover, all statements herein reciting principles, aspects, and embodiments of the present disclosure, as well as specific examples, are intended to encompass equivalents thereof.

FIG. 5 illustrates an exemplary survey to collect feedback of the patient using a user interface of the mobile device, according to an embodiment of the present disclosure.

FIG. 10 illustrates exemplary notifications from an application based on the wear times of the wearable medical device by a patient, according to an embodiment of the present disclosure.

FIG. 11 illustrates an exemplary report depicting compliance status and other statistics of a patient, according to an embodiment of the present disclosure.

DETAILED DESCRIPTION

Figure 1:
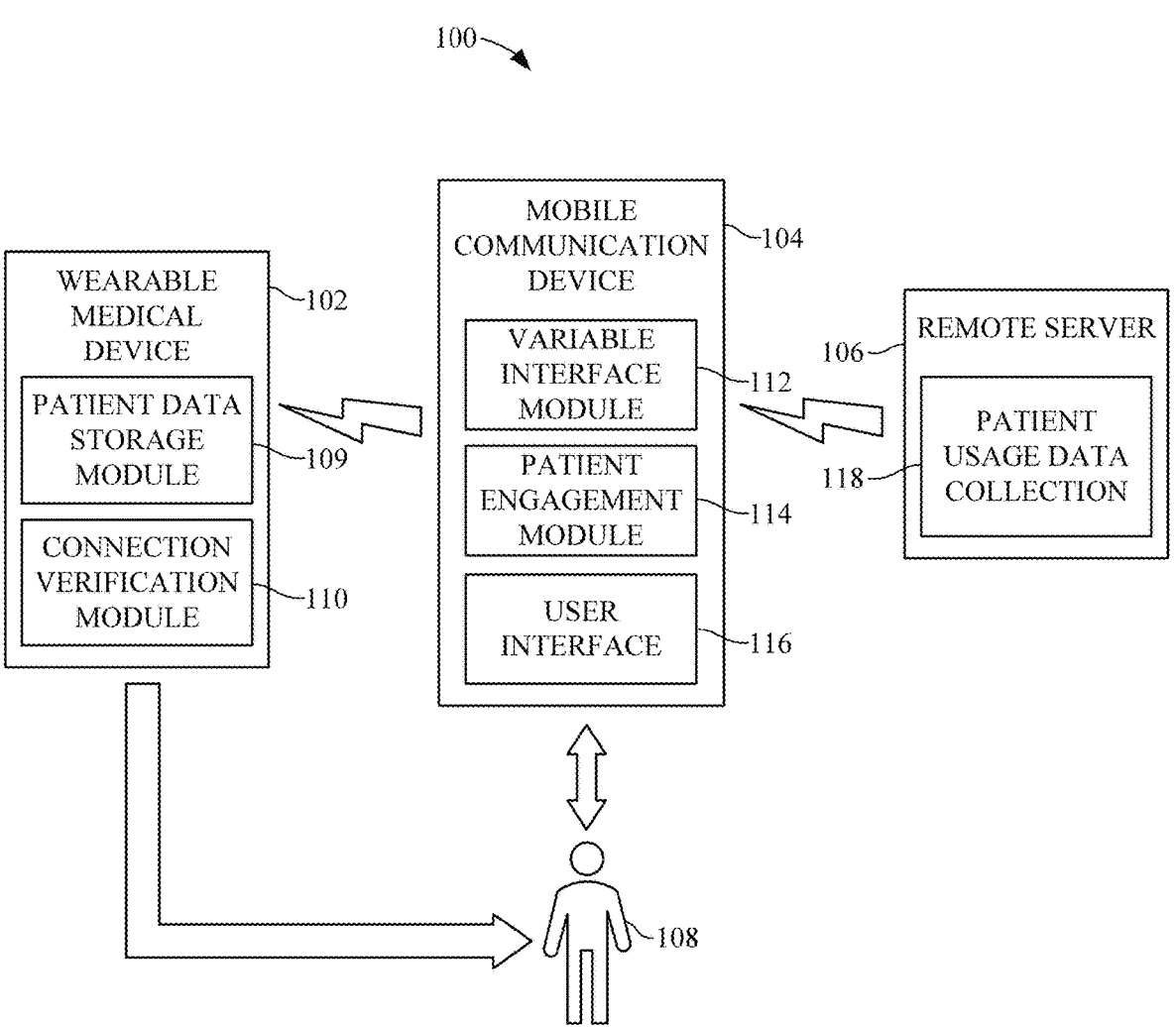
FIG. 1 depicts components of a medical system along with the connections therebetween, according to an embodiment of the present disclosure.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures or methods associated with the medical system has not been shown or described in detail to avoid unnecessarily obscuring descriptions of the embodiments.

Unless the context indicates otherwise, throughout the specification and claims which follow, the word "comprise" and variations thereof, such as, "comprises" and "comprising" are to be construed in an open, inclusive sense that is as "including, but not limited to." Further, the terms "first," "second," and similar indicators of the sequence are to be construed as interchangeable unless the context clearly dictates otherwise.

Reference throughout this specification to "one aspect" or "an aspect" means that a particular feature, structure, or characteristic described in connection with an embodiment is included in at least one aspect. Thus, the appearances of the phrases "in one aspect" or "in an aspect" in various places throughout this specification are not necessarily all referring to the same embodiment. Furthermore, the particular features, structures, or characteristics may be combined in any suitable manner in one or more aspects.

As used in this specification and the appended claims, the singular forms "a," "an," and "the" include plural referents unless the content clearly dictates otherwise. It should also be noted that the term "or" is generally employed in its broadest sense, that is, as meaning "and/or" unless the content clearly dictates otherwise.

In situations where a patient is not engaged or paired with a mobile communication device that relays patient data from a wearable medical device to one or more servers, there may be problems related to delay in response time or lack of response. For example, in case of an emergency such as a cardiac event associated with the patient, a slight delay in responding to the emergency may be fatal. Therefore, there is a need to improve engagement of the patient with the mobile communication device, to enable the one or more remote servers to respond to emergencies efficiently and effectively.

Upon consistent pairing between the patient and the mobile communication device, the patient data is relayed without delay to the one or more remote servers. The relayed patient data is provided by the one or more remote servers to medical service providers that are better equipped to take prompt action in life-threating situations.

The embodiments of the present disclosure relate to provision of an interactive survey-based variable user interface (UI) to optimize the mobile communication device to the patient's needs and technology background. For example, in some embodiments, the interactive survey may include a series of questions that the patient may answer in accordance with a level of comfort of using the mobile communication device and options to customize font size, button size, sentence complexity, and colors of the UI. The patient may have an option to view the series of questions via a visual interface or may select an option to hear the questions via an audio interface.

The interactive survey, within the context of the present disclosure, is not limited to mere selection of features like font size, button size, sentence complexity, and colors of the UI on settings screen of an application running on the mobile communication device. Instead, the interactive survey enables interaction between the mobile communication device and the patient via a survey, such as in form of a series of questions that are being presented to the patient. The answers or responses to the questions, in turn, enable configuration or re-configuration of the UI elements to enhance patient engagement with the mobile communication device. The details of the interactive survey are described later in accompanying figures. Further, the inputs provided by the patient in response to the survey questions enable customization of the UI to match patient's preferences.

Due to the customization of the UI associated with the mobile communication device, patient's comfort levels in using the mobile communication device may increase. Advantageously, increased patient comfort levels may help in increasing the number of patients that are paired with the respective mobile communication devices. As a result of more patients being paired, the accuracy of data at the one or more remote servers is likely to be improved. Further, with the increased patient engagement with the respective mobile communication devices, the likelihood of patients wearing the wearable medical device for a recommended amount of time per day is also increased. Additionally, consistent pairing or engagement of the patient directly with the wearable medical device or indirectly via the mobile communication device may facilitate verification of the patient usage of the wearable medical device in near real time.

In some embodiments, the mobile communication device may be configured with the survey functionality and the patient is provided with such dedicated device, while in other embodiments, the functionality may be in a download-able application (or app) to be loaded and run on the personal mobile communication device of the patient. In some embodiments, there may be several additional features to encourage patients to use the mobile communication device and/or act as incentives for the patients to keep the mobile communication device consistently paired.

FIG. 1 depicts components of a medical system 100 along with the connections therebetween. The medical system 100 includes a wearable medical device 102, a mobile communication device 104, and a remote server 106. In the present disclosure, the mobile communication device 104 may be commonly referred to as "mobile device." Further, for the sake of brevity, the remote server 106 is indicated as a single remote server 106 in FIG. 1, however there may be multiple remote servers, either at same geographical location or at different geographical locations operating and coordinating in a distributed manner to achieve server functionality, without limitation. Depending on the context, "remote server" and "one or more remote servers" are being used in the present disclosure.

As shown in FIG. 1, a patient 108 may interact with the mobile communication device 104 for relaying patient data from the wearable medical device 102 to the remote server 106. The patient 108 can be a user 108, also known as a wearer 108 of the wearable medical device 102. The user 108 may also be a local rescuer at the scene, such as a bystander who might help the patient 108. The user 108 may also be a trained person or another person who might be remotely located as a trained caregiver in communication with the wearable medical device 102. The present disclosure refers to the patient 108 as the user 108 based on the context, and should be interpreted accordingly.

Referring to FIG. 1, in some embodiments, the wearable medical device 102 includes a patient data storage module 109 and a connection verification module 110. The patient data storage module 109 is operable to store patient data once the wearable medical device 102 is worn by the patient 108. The patient data includes patient physiological param-eters, system parameters, and/or environmental parameters associated with the patient 108. One or more of the param-eters included in the patient data may be utilized by the wearable medical device 102 to detect a cardiac condition (e.g., arrhythmia) related to the patient 108, and to determine if the patient 108 is in need of a therapy based on the detected cardiac condition. The details of the aforemen-tioned parameters are described later with respect to FIG. 4.

The connection verification module 110 may be config-ured to detect if the mobile communication device 104 is paired with the wearable medical device 102. The connec-tion verification module 110 may alert the patient 108 when the mobile communication device 104 is not paired. As used herein within the context of the present disclosure, "paired" and "pairing" includes establishing a wireless connection between the wearable medical device 102 and the mobile communication device 104 using a wireless technology such as but not limited to Bluetooth, Wi-fi, Zigbee, and the like. It is apparent that the connection between the wearable medical device 102 and the mobile communication device 104 may be established when the mobile communication device 104 is powered on and lies in a predetermined range of the wearable medical device 102. Exemplary range includes a range of 10 meters but can be extended to other values by reducing interference, using range extenders and/or amplifiers, and other means without limitation. In certain embodiments, the connection verification module 110 may be configured to provide an audible or visual alert on the wearable medical device 102 when the wearable medical device is being worn by the patient 108 and communication has not been established between the wearable medical device 102, the mobile communication device 104, and the remote server 106 for a disconnection duration. In some examples, the disconnection duration can refer to a duration of disconnection between the wearable medical device 102 and the mobile communication device 104. The disconnec-tion duration, for example, may be set as a value between 30 minutes to 24 hours. There may be scenarios when a prompt is presented to the patient 108 as soon as a disconnection is detected between the wearable medical device 102 and the mobile communication device 104, to ensure that the com-munication between the aforementioned devices is re-estab-lished. The disconnection may occur in various situations such as but not limited to when the patient 108 is not wearing the wearable medical device 102, the patient 108 left or forgot the mobile communication device 104 at some place, when the mobile communication device 104 is not in a range of the wearable medical device 102, the patient turned off the setting responsible for pairing (e.g., Bluetooth setting), the mobile communication device 104 slipped into a low power mode causing the wireless connections to turn off, and the like.

Further, in some embodiments, the connection verifica-tion module 110 may provide a confirmation of a connection between the wearable medical device 102 and the mobile communication device 104 using at least one of visual, audio, and/or notification indication on the mobile commu-nication device 104. In other embodiments, the wearable medical device 102 may directly determine the pairing between the wearable medical device 102 and mobile com-munication device 104, in absence of the connection veri-fication module 110. The wearable medical device 102 collects the patient data from the body of the patient or user 108 wearing the wearable medical device 102 and analyzes the patient data to provide vitals of the patient 108. The vitals of the patient 108 may include but are not limited to body temperature, pulse rate, respiration rate, blood pressure etc. Examples of the wearable medical device 102 may include a wearable cardioverter defibrillator (WCD), wear-able cardiac monitoring device, and other similar wearable medical devices.

The mobile communication device 104 includes at least one processor and a display, and details regarding the components of the mobile communication device 104 will be explained later in FIG. 6. The mobile communication device 104 is configured to establish communication between the wearable medical device 102 and the remote server 106. The mobile communication device 104, in some embodiments, includes a variable interface module 112, a patient engagement module 114, and a user interface 116. Examples of the mobile communication device 104 may include but are not limited to phone, laptop, smartphone, tablet device, wearable mobile device, and the like.

The variable interface module 112 of the mobile communication device 104 modifies aspects of the user interface 116 in response to a patient survey. In some embodiments, the variable interface module 112 is a software module run by at least one processor of the mobile communication device 104, which causes the user interface 116 of the mobile communication device 104 to conduct the patient survey by visually displaying survey questions on the user interface 116. In some other embodiments, the user interface 116 provides the survey questions audibly using a speaker of the user interface 116 and receives and stores responses via a microphone of the user interface 116. The user interface 116 may also receive patient's responses to the survey questions, which the variable interface module 112 can store and process for adjusting various parameters of the user interface 116. In embodiments, the variable interface module 112 then reconfigures the user interface 116 according to survey responses. In certain embodiments, the variable interface module 112 may provide previews of the reconfigured user interface 116 to the patient 108. The patient 108, in some embodiments, may then accept or decline the reconfiguration via the user interface 116. Therefore, the variable interface module 112 can help improve or encourage patient usage of the mobile communication device 104 for a patient 108 that is uncomfortable with technology and/or has difficulty in using the mobile communication device 104 (e.g., due to diminished vision, hearing, manual dexterity, etc.). As a result, the consistency of pairing the mobile communication device 104 with the wearable medical device 102 is enhanced.

The patient engagement module 114 of the mobile communication device 104, in some embodiments, is a software module run by at least one processor of the mobile communication device 104. The patient engagement module 114 may enable the mobile communication device 104 to provide features to encourage patient engagement with the mobile communication device 104. The engagement can result in more consistent pairing between the mobile communication device 104 and the wearable medical device 102 because the patient 108 will be using both the wearable medical device 102 and the mobile communication device 104, which allows these devices to be in close proximity. Increased patient engagement with the mobile communication device 104 causes an increase in a duration of established communication between the mobile communication device 104, the wearable medical device 102, and the remote server 106. As a result, timely communication of the patient data from the patient data storage module 109 of the wearable medical device 102 to the mobile communication device 104 is enabled. The mobile communication device 104 can communicate the patient data to the remote server 106, which will be explained in the subsequent embodiments.

In some embodiments, the patient engagement module 114 may be configured to help implement one or more of several features designed to increase patient engagement with the mobile communication device 104, in the mobile communication device 104. The one or more patient engagement features may include but are not limited to interactive games, notifications, programmable timed messages, photos, music, podcasts, and news stories. Games may include, for example, crosswords, wordles, and sudoku to encourage patient interest and help the patient(s) 108 become more comfortable with usage of the mobile communication device 104. In some embodiments, games may include flashcards and quizzes with questions about the wearable medical device 102. The question(s), as a non-limiting example, may include "What should you do when you get a Heart Alert?", that may serve to familiarize the patient 108 with the mobile communication device 104 and encourage consistent pairing and patient comfortability with and knowledge around the wearable medical device 102 itself. The notifications may be set up from news, sports, or social media websites. Further, a daily (or other perhaps programmable time interval) message such as "thought for the day" may be set up to encourage the patient's daily usage of the mobile communication device 104. A photo album that the patient 108 can engage with, and to which the family and friends of the patient 108 can send photos to the mobile communication device 104 for the patient 108 to see, may be created to increase patient engagement. Further, the patient 108 may be provided the ability to play music, podcasts, or news from the mobile communication device 104.

In addition to the patient engagement features described above, the respective abilities of the mobile communication device 104 and the wearable medical device 102 may be utilized to increase patient engagement. As an example, the ability of the mobile communication device 104 to detect patient usage and change the user interface 116 if usage is less. As another example, the ability of the wearable medical device 102 to detect patient usage and prompt the patient 108 to pair the mobile communication device 104 if the mobile communication device 104 has not been paired that day, which is a function of the connection verification module 110. Further, in order to engage the patient 108, badges and awards can be earned by the patient 108 for consistent usage of the mobile communication device 104.

In some embodiments, the patient engagement module 114 may include a feature for the patient(s) 108 to earn "heart rewards" for consecutive wear days and amount of time per day the wearable medical device 102 is worn. Patients 108 may reach different "compliance status tiers" based on the amount of time the respective wearable medical device 102 is worn, starting from the lowest "Red" tier for wearing the wearable medical device 102 for 12 hours per day, as an example, to the highest "Platinum" tier for wearing the wearable medical device 102 for the recommended 22.5 hours per day, as an example. A wear time of the wearable medical device 102 (or WCD wear time) for each compliance status tier may be predetermined or may be determined dynamically based on the wear time data of a pool of patients in real time, without limitation. In further embodiments, the patients 108 may compete on a compliance status tier leaderboard, encouraging the patients 108 to consistently wear the wearable medical device 102 for the recommended amount of time each day. It shall be noted that the recommended amount of time for wearing the wearable medical device 102 per day may be predetermined based on health condition of the respective patient 108 or may be dynamically updated/determined based on change in health condition of the respective patient 108. In some embodiments, the earning of heart rewards may trigger a heart alert for the patient 108 on the user interface 116. In other embodiments, the heart rewards may correspond to heart alerts for the patient 108. Details regarding the heart rewards and compliance status tiers will be explained in subsequent embodiments depicted in FIGS. 6-11.

Although the embodiments above are described with respect to the patient engagement module 114, however there may be embodiments where the patient engagement module 114 is absent.

The medical system 100 further includes the remote server 106, which collects the patient data or patient information. In an embodiment, the remote server 106 may be implemented using a remote patient data platform such as Kestra CareStation® which is developed and offered by Kestra Medical Technologies, Inc. of Kirkland, Washington. In some embodiments, the remote server 106 may be implemented using a web service such as Amazon Web Services®, Microsoft Azure®, Google Cloud Platform, or any other cloud platform provider. In other embodiments, the remote server 106 may be implemented using one or more server devices operated by a provider of the wearable medical device 102. The remote server 106 collects patient data, including patient usage data (indicated as patient usage data collection 118 in FIG. 1), from the patient data storage module 109 of the wearable medical device 102 via the mobile communication device 104. The patient usage data collection 118 may be used in ensuring product effectiveness (e.g., the wearable medical device 102 is optimally worn for at least 23 hours per day) and in verifying the patient usage of the product for insurance billing purposes.

In embodiments, the remote server 106 may be configured to collect data including but not limited to patient vitals, electrocardiogram (ECG) of arrhythmias detected by the wearable medical device 102, and location information of the wearable medical device 102 or the mobile communication device 104. Further, in some embodiments, the remote server 106 makes the aforementioned collected data accessible to a physician of the patient 108 and members of a clinical team that are remotely located. In an embodiment, the remote server 106 is configured to analyze patient data and/or provide the patient data to a medical service provider for taking an appropriate action related to cardiac activity of the patient 108. As an example, the remote server 106 may be configured to alert a first responder of a medical emergency when the patient data from the wearable medical device 102 indicates that the patient 108 is experiencing the medical emergency. The first responder may include but is not limited to nurse, compounder, representative of the patient 108, and the like. Further, as another example, the embodiments of the remote service provided by the remote server 106 may enable a doctor and/or other clinicians or authorized personnel to remotely review the patient data from the wearable medical device 102 in a timely manner. Based on the received patient data, potentially life-saving assistance may be provided to the patient 108 by the doctors, clinicians, and/or authorized personnel such as by contacting or visiting the patient 108, calling an emergency helpline number or contacting a local emergency medical system (EMS), requesting family members to visit the patient 108, and the like.

In exemplary embodiments, the components of the medical system 100 described above may be implemented as disclosed in U.S. Pat. No. 8,838,235, incorporated herein by reference for all purposes, with embodiments of additional modules within each component as described above.

As shown in FIG. 1, the lightning icons between the wearable medical device 102 and the mobile communication device 104, and between the mobile communication device 104 and the remote server 106 indicate a (successful) connection therebetween. In an embodiment, when the mobile communication device 104 is successfully paired with the wearable medical device 102, then the mobile communication device 104 can receive patient data from the patient data storage module 109 of the wearable medical device 102, and subsequently transmit the patient data from the patient data storage module 109 of the wearable medical device 102 to the remote server 106 via the mobile communication device 104.

The interaction between the patient 108 and components of the medical system 100 is indicated by arrows between the patient 108 and respective devices in FIG. 1. Specifically, information flow between the wearable medical device 102, the mobile communication device 104, and the remote server 106 is indicated by the arrows. A single head arrow between the wearable medical device 102 and the patient 108 indicates that in some embodiments, the wearable medical device 102 can notify the patient 108 if the wearable medical device 102 detects that the mobile communication device 104 is unpaired and/or disconnected from the wearable medical device 102. Further, a double-headed arrow between the mobile communication device 104 and the patient 108 indicates that the patient 108 can interact with the mobile communication device 104, and the mobile communication device 104 can also interact with and respond to the patient 108 simultaneously. An example of the interaction between the patient 108 and the mobile communication device 104 is during setup of the medical system 100. During the setup, the patient 108 responds to a survey about the user interface 116 and the variable interface module 112 of the mobile communication device 104 can alter the user interface 116 in response. The details of the survey will be discussed later in FIG. 5. In some embodiments, the mobile communication device 104 can also interact with the patient 108 if the mobile communication device 104 detects less patient usage of the wearable medical device 102.

Figure 2:
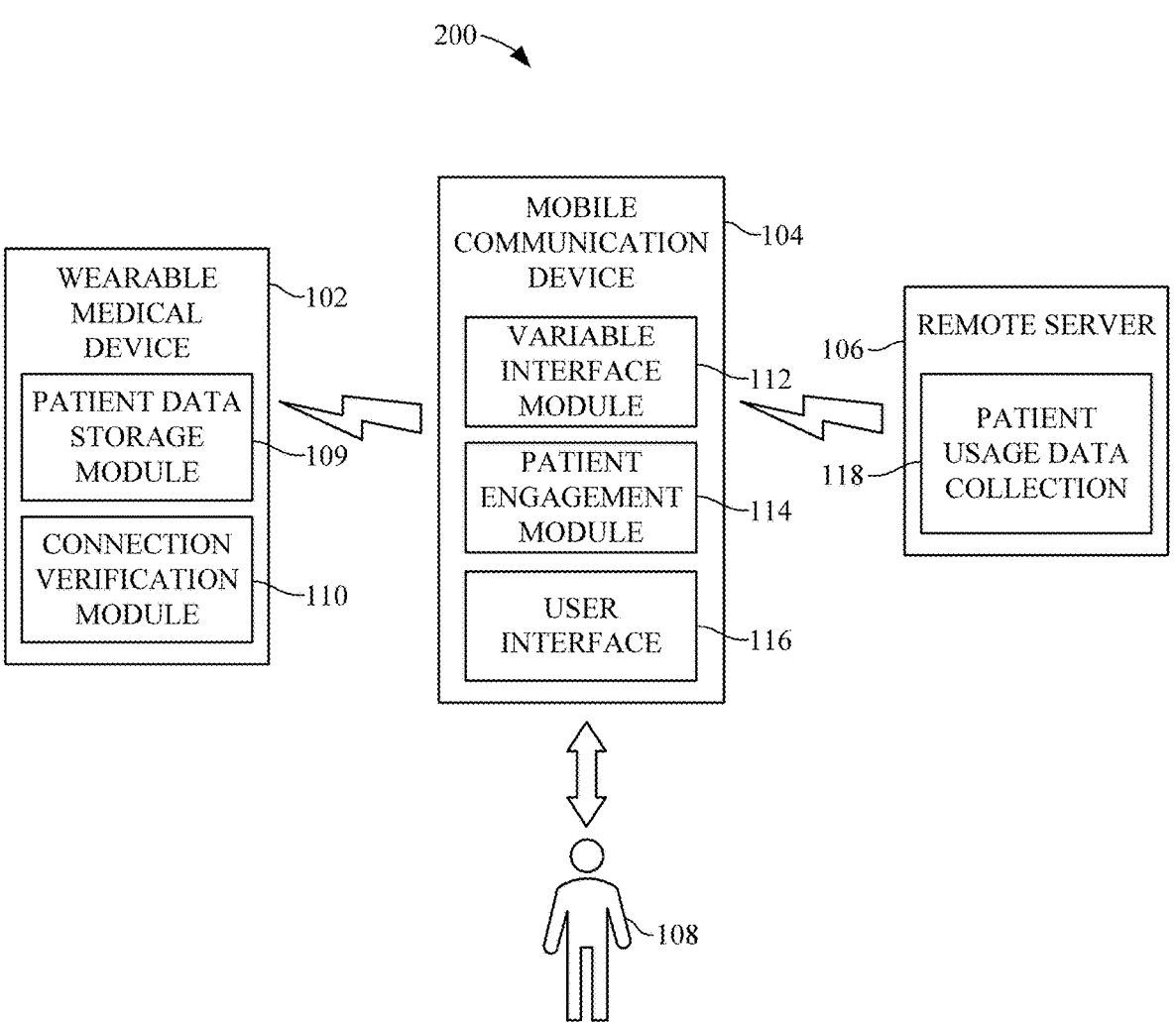
FIG. 2 depicts components of a medical system in a situation in which a patient keeps the mobile communication device paired with the wearable medical device, according to an embodiment of the present disclosure.

FIG. 2 depicts components of a medical system 200 in a situation in which the patient 108 keeps the mobile communication device 104 paired with the wearable medical device 102, with successful connections between the mobile communication device 104 and both the wearable medical device 102 and the remote server 106, respectively. FIG. 2 is described in conjunction with FIG. 1, and since the components of FIG. 2 are same as components of FIG. 1, hence the description of same components is not repeated for the sake of brevity. FIG. 2 differs from FIG. 1 as the information flow from the wearable medical device 102 to the patient 108 is missing. The absence of information flow between the wearable medical device 102 and the patient 108 may occur when the wearable medical device 102 is not connected to the patient 108 such as when the patient 108 does not choose to wear or forgets to wear the wearable medical device 102. In such a situation, the patient data can be communicated from the wearable medical device 102 to the remote server 106 via the mobile communication device 104 in a manner that is similar to that described in the aforementioned U.S. Pat. No. 8,838,235.

In an exemplary embodiment related to FIG. 2, if the patient 108 chooses not to wear the wearable medical device 102 or unfastens the wearable medical device 102 for being uncomfortable or forgets to wear the wearable medical device 102, then the patient data that is most recently available or previously synchronized with the wearable medical device 102 may be transmitted to the remote server 106 via the mobile communication device 104. This may be understood by an example such as in case of mild cardiac activity suffered by the patient 108 before unfastening the wearable medical device 102, such information (or patient data) related to the mild cardiac activity may be transmitted to the remote server 106, whereby medical service providers can take the appropriate action accordingly. In an embodiment, the synchronization between the wearable medical device 102 and the mobile communication device 104, and the synchronization between the mobile communication device 104 and the remote server 106 occurs after a predetermined time duration. The predetermined time duration may be configurable by the patient 108 or any user or the medical service provider via the remote server 106.

Figure 3:
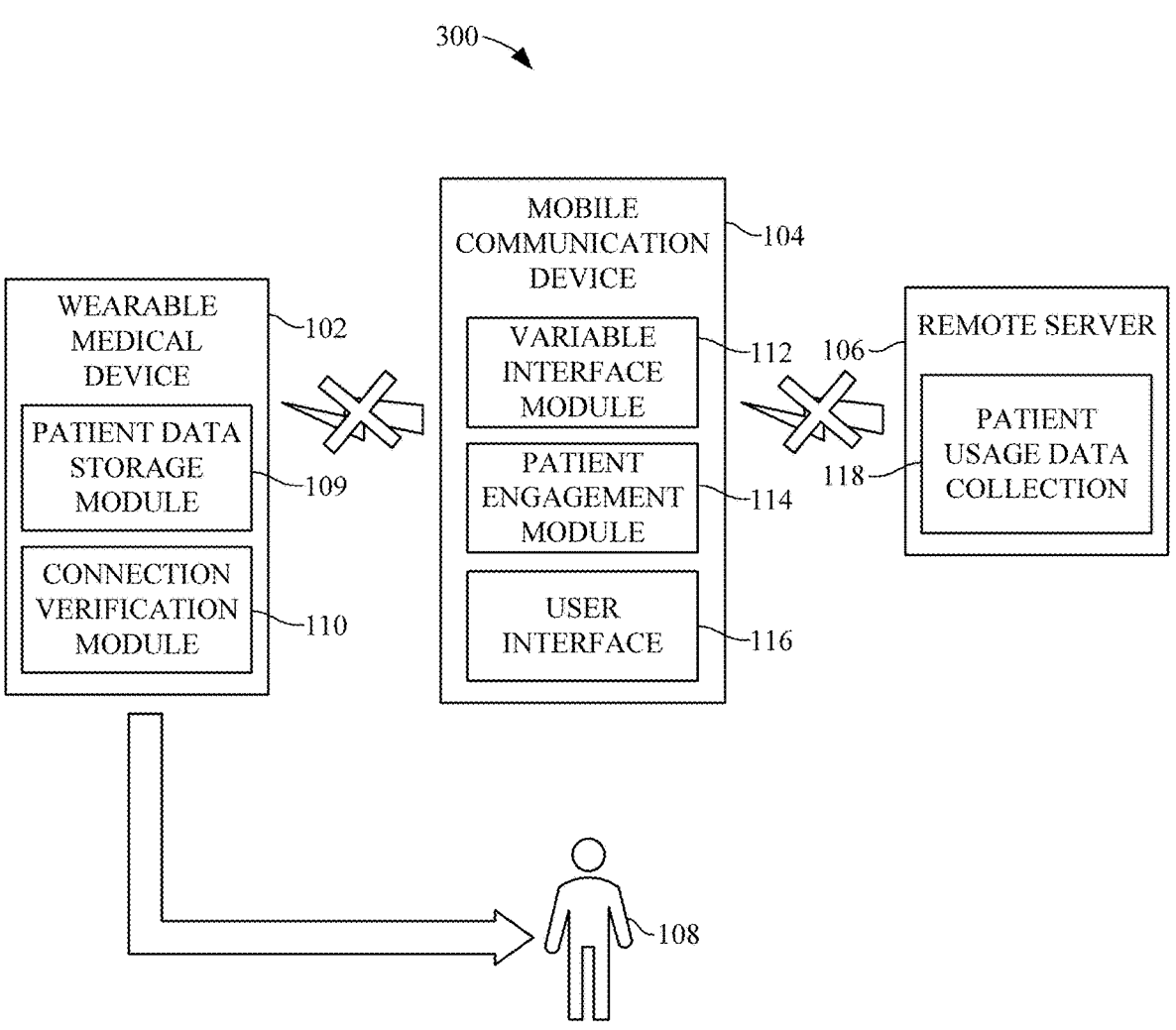
FIG. 3 depicts components of a medical system in a situation in which the patient does not keep the mobile communication device paired with the wearable medical device, according to an embodiment of the present disclosure.

FIG. 3 depicts components of a medical system 300 in a situation in which the patient 108 does not keep the mobile communication device 104 paired with the wearable medical device 102. In this situation, the patient data stored in the mobile communication device 104 does not transmit from the mobile communication device 104 to the remote server 106 and the patient data from the wearable medical device 102 is not transmitted to the mobile communication device 104. The components of FIG. 3 are the same as the components of FIG. 1, with the absence of information flow between the mobile communication device 104 and the patient 108. The non-paired connection (cross icon) represents the loss of communication between the wearable medical device 102 and the mobile communication device 104, and between the mobile communication device 104 and the remote server 106.

In some embodiments, a successful connection may exist between the mobile communication device 104 and the remote server 106, however there may be an unsuccessful connection between the wearable medical device 102 and the mobile communication device 104. When communication between the wearable medical device 102, the mobile communication device 104, and the remote server 106 is not established, there may be no patient usage data collection 118 at the remote server 106. Accordingly, there will be no patient data transmitted from the wearable medical device 102 to the remote server 106. In response to detecting that pairing between the wearable medical device 102 and the mobile communication device 104 is not maintained, in some embodiments, the connection verification module 110 is configured to cause the wearable medical device 102 to provide an alert to the patient 108 to remind them to pair the mobile communication device 104. The alert is an audible alert or visual alert provided on the wearable medical device 102. For example, the alert can be an audible prompt addressed to the patient 108 to ensure that the wearable medical device 102 is connected to the mobile communication device 104. In another example, the alert can be a visual alert to the patient 108 through the wearable medical device 102 to indicate that there is no connection established between the wearable medical device 102 and the mobile communication device 104. In yet another example, the wearable medical device 102 may alert to the patient 108 via an audible or visual prompt to ensure that the mobile communication device 104 is turned on and has sufficient battery charge. Although few examples of audible and visual alerts are described herein, however the present disclosure is not limited to these alerts and may include other forms of alerts as well without departing from the scope of the present disclosure. In some embodiments, the patient 108 can disable the alerts from the wearable medical device 102. In other embodiments, the patient 108 can configure or customize the wearable medical device 102 to only send pairing alerts under certain conditions. The customizations may include but are not limited to a minimum amount of disconnection time or threshold duration that must elapse before the wearable medical device 102 can send an alert or a certain period of time during which the wearable medical device 102 cannot send alerts (e.g., sleeping hours).

In certain embodiments, an alert or prompt may be presented on either the wearable medical device 102 or the mobile communication device 104 when a disconnection duration threshold or disconnection consistency threshold is exceeded. For example, when the patient 108 is connected or interacts with the mobile communication device 104 but is not wearing the wearable medical device 102 for a certain duration (e.g., disconnection duration threshold or disconnection consistency threshold), the alert or prompt may be presented to the patient 108 on the mobile communication device 104 to re-establish the connection with the wearable medical device 102. However, when the patient 108 is wearing the wearable medical device 102 but is not connected to the mobile communication device 104 for a certain duration (disconnection duration threshold or disconnection consistency threshold), then the alert or prompt may be presented to the patient 108 on the wearable medical device 102 to re-establish the connection with the mobile communication device 104. The disconnection duration threshold may refer to a minimum amount of time for which the wearable medical device 102 and the mobile communication device 104 are not communicatively connected. As an example, the value of disconnection duration threshold may be set between 30 minutes to 24 hours. The disconnection consistency threshold may refer to a total amount of disconnections during a period of time for which the wearable medical device 102 and the mobile communication device 104 are not consistently paired. For example, the disconnection consistency threshold can be about 1, 2, 3, 4, 5, 6, 7, 8, 9, 10, 11, 12, 13, 14, 15, 16, 17, 18, 19, 20 or more disconnections between the wearable medical device 102 and the mobile communication device 104 per 24 hour period. In some examples, the disconnection consistency threshold can be a total number of disconnections during a period of time that the patient 108 is wearing the wearable medical device 102. For example, the patient 108 may wear the wearable medical device 102 for a number of hours per day and the disconnection consistency threshold may be about 1, 2, 3, 4, 5, 6, 7, 8, 9, 10, 11, 12, 13, 14, 15, 16, 17, 18, 19, 20, or more disconnections between the wearable medical device 102 and the mobile communication device 104 while the patient 108 is wearing the wearable medical device 102. In some examples, the patient 108 may wear the wearable medical device 102 for less than 10 hours per day, about 10 hours to about 12 hours per day, about 12 hours to about 14 hours per day, about 14 hours to about 16 hours per day, about 16 hours to about 18 hours per day, about 18 hours to about 20 hours per day, about 20 hours to about 22 hours per day, or about 22 hours to about 24 hours per day.

Figure 4:
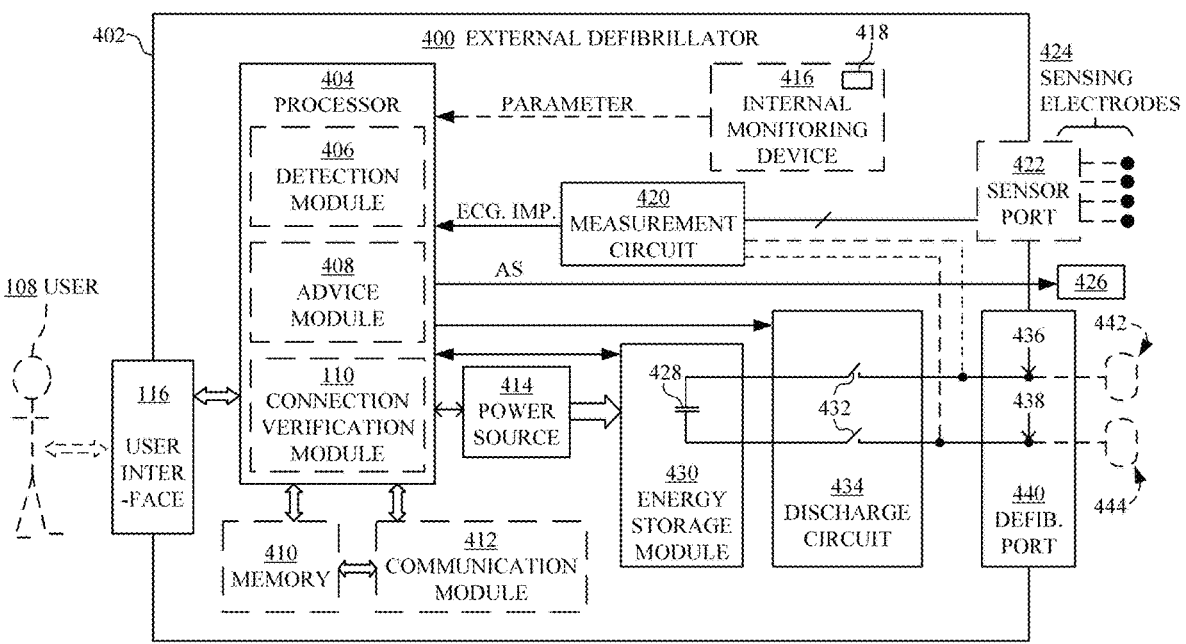
FIG. 4 illustrates a block diagram of an external defibrillator, according to an embodiment of the present disclosure.

FIG. 4 illustrates a block diagram showing components of an external defibrillator 400, according to an embodiment of the present disclosure. FIG. 4 is described in conjunction with previous figures. The external defibrillator 400 depicts one of the implementations of the wearable medical device 102, which may be a WCD, for example.

The external defibrillator 400 is intended for the patient 108 who would be wearing the wearable medical device 102. In embodiments, the external defibrillator 400 may be used by a user 108 or a local rescuer at the scene who may offer assistance or a trained person. Without limitation, the user 108 or rescuer may be remotely located and in communication with the wearable medical device 102. The embodiment of FIG. 4 is described herein with respect to the patient 108; however, the embodiment is applicable to user 108, rescuer, or trained person without limitation.

The external defibrillator 400 includes the user interface 116, a housing 402, a processor 404, a memory 410, a communication module 412, a power source 414, an internal monitoring device 416, a motion detector 418, a measurement circuit 420, a sensor port 422, sensing electrodes 424, a capacitor 428, an energy storage module 430, one or more switches 432, a discharge circuit 434, and a defibrillation port 440. The defibrillation port 440 further includes a couple of electrical nodes 436 and 438. The processor 404 further includes a detection module 406, an advice module 408, and the connection verification module 110.

The user interface 116 may include output devices, which can be visual, audible, or tactile, for communicating with the patient 108 by outputting images, sounds, or vibrations. Images, sounds, vibrations, and anything that can be perceived by the patient 108 can also be called human-perceptible indications (HPIs). For example, an output device can be a light, or a screen to display what is sensed, detected and/or measured, and provide visual feedback to the patient 108 for their resuscitation attempts, and so on. Another example of output device can be a speaker, which can be configured to issue voice prompts, beeps, loud alarm sounds and/or words to warn bystanders, etc. The user interface 116 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

The internal monitoring device 416 is called an "internal" device because it is incorporated within the housing 402. The internal monitoring device 416 can sense or monitor patient parameters such as patient physiological parameters, system parameters, and/or environmental parameters, all of which can be called as the patient data. The internal monitoring device 416 may include one or more sensors.

The patient physiological parameters may include, for example and without limitation, those physiological parameters that can be of any help in detecting by the wearable medical device 102 whether or not the patient 108 is in need of therapy (e.g., a shock) or other intervention or assistance. The patient physiological parameters may also optionally include the medical history of the patient 108, event history, and the like. Examples of the patient physiological parameters include ECG, blood oxygen level, blood flow, blood pressure, blood perfusion, pulsatile change in light transmission or reflection properties of perfused tissue, heart sounds, heart wall motion, breathing sounds, and pulse. Accordingly, the internal monitoring device 416 may include one or more sensors configured to acquire physiological signals of the patient 108. Examples of such sensors or transducers may include but are not limited to one or more electrodes to detect ECG data, a perfusion sensor, a pulse oximeter, a device for detecting blood flow (e.g., a Doppler device), a sensor for detecting blood pressure (e.g., a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and the like. In view of the present disclosure, it will be appreciated that such sensors can help detect the patient's pulse, and can therefore be also called as pulse detection sensors, pulse sensors, and pulse rate sensors. In addition, a person skilled in the art may implement other ways of performing pulse detection.

In some embodiments, the local parameter is a trend that can be detected in a monitored physiological parameter of the patient 108. A trend can be detected by comparing values of parameters at different times over short and long terms. Parameters whose detected trends can particularly help a cardiac rehabilitation program include: a) cardiac function (e.g., ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and the like. Once a trend is detected, the trend can be stored and/or reported via a communication link, along with a warning if warranted. From the report, a physician monitoring the progress of the patient 108 will know about a condition that is either not improving or deteriorating.

Further, patient state parameters may be recorded by the internal monitoring device 416. The patient state parameters include recorded aspects of the patient 108, such as motion, posture, whether they have spoken recently and maybe also what they said, and the like, and optionally the history of these parameters. In some embodiments, one of these monitoring devices could include a location sensor such as a Global Positioning System (GPS) location sensor. Such a sensor can detect the location, and a speed can be detected as a rate of change of location over time. Many motion detectors output a motion signal that is indicative of the motion of the detector, and thus of the body of the patient 108. The patient state parameters can be very helpful in narrowing down the determination of whether sudden cardiac arrest (SCA) is indeed taking place for the patient 108.

In embodiments, the motion detector 418 can be implemented within the internal monitoring device 416. The motion detector can be made in many ways, for example, by using an accelerometer. In this example, the motion detector 418 may be implemented within the internal monitoring device 416. The motion detector 418 of the wearable medical device 102, according to embodiments, can be configured to detect a motion event. A motion event can be defined as convenient, for example, a change in motion from a baseline motion or rest, etc. In such cases, a sensed patient parameter is motion.

The system parameters can include system identification, battery status, system date and time, reports of self-testing, records of data entered, records of episodes and intervention, and the like. In response to the detected motion event, the motion detector 418 may render or generate, from the detected motion event or motion, a motion detection input that can be received by a subsequent device or functionality.

Further, the environmental parameters can include ambient temperature and pressure. Moreover, a humidity sensor may provide information as to whether it is likely raining or not. Presumed patient location could also be considered an environmental parameter. The patient location could be presumed, if the internal monitoring device 416 includes a GPS location sensor as discussed above, and if it is presumed that the patient 108 is wearing the wearable medical device 102.

The defibrillation port 440 can be a socket in the housing 402 and includes electrical nodes 436, 438. Leads of defibrillation electrodes 442, 444 can be plugged into the defibrillation port 440, so as to make electrical contact with nodes 436, 438, respectively. In some embodiments, the defibrillation electrodes 442, 444 may be connected continuously to the defibrillation port 440, instead. Either way, the defibrillation port 440 can be used for guiding, via electrodes, to the patient 108 (or wearer) at least some of the electrical charge that has been stored in the energy storage module 430. The electric charge will be the shock for defibrillation, pacing, and the like. The provision of shock for defibrillation and/or pacing may be referred to as therapy treatment. Since the defibrillation electrodes 442, 444 facilitate provision of therapy to treat the heart of the patient 108, the defibrillation electrodes 442, 444 may be referred to as therapy electrodes.

The external defibrillator 400 may optionally include a sensor port 422 in the housing 402, which is also sometimes known as an ECG port. The sensor port 422 can be adapted for plugging in the sensing electrodes 424, which are also known as ECG electrodes and ECG leads. In some embodiments, the sensing electrodes 424 may be connected continuously to the sensor port 422, instead. The sensing electrodes 424 are types of transducers that can help sense an ECG signal, e.g. a 12-lead signal, or a signal from a different number of leads, especially if they make good electrical contact with the body of the patient 108 and in particular with the skin of the patient 108. As with the defibrillation electrodes 442, 444, a support structure (not shown) of the wearable medical device 102 can be configured to be worn by the patient 108 so as to maintain the sensing electrodes 424 on the body of patient 108. For example, the sensing electrodes 424 can be attached to the inside of the support structure for making good electrical contact with the patient 108, similar to the defibrillation electrodes 442, 444.

Optionally, the wearable medical device 102, according to embodiments, also includes a fluid that may be deployed automatically between the electrodes (referring collectively to the defibrillation electrodes 442, 444 and the sensing electrodes 424) and the patient's skin. The fluid can be conductive, such as by including an electrolyte, for establishing a better electrical contact between the electrodes and the skin. Electrically, when the fluid is deployed, the electrical impedance between each electrode and the skin is reduced. The fluid may be in the form of a low-viscosity gel, so that the fluid does not flow away, after being deployed, from the location it is released near the electrode. The fluid can be used for both defibrillation electrodes 442, 444, and for the sensing electrodes 424.

The fluid may be initially stored in a fluid reservoir, not shown in FIG. 4. Such a fluid reservoir can be coupled to the support structure. In addition, the wearable medical device 102, according to embodiments, further includes a fluid deploying mechanism 426. The fluid deploying mechanism 426 can be configured to cause at least some of the fluid to be released from the reservoir and be deployed near one or both of the patient locations to which the defibrillation electrodes 442, 444 are configured to be attached to the patient 108. In some embodiments, the fluid deploying mechanism 426 is activated prior to the electrical discharge responsive to receiving activation signal AS from the processor 404.

In some embodiments, the measurement circuit 420 may include components that may function together with sensors or transducers. The measurement circuit 420 senses one or more electrical physiological signals of the patient 108 from the sensor port 422. Even if the external defibrillator 400 lacks the sensor port 422, the measurement circuit 420 may optionally obtain physiological signals through the electrical nodes 436, 438 instead, when the defibrillation electrodes 442, 444 are attached to the patient 108. In such cases, the input reflects an ECG measurement. The patient parameter can be an ECG as an example, which can be sensed as a voltage difference between the defibrillation electrodes 442, 444. In addition, the patient parameter can be an impedance, which can be sensed between the defibrillation electrodes

442, 444 and/or between the connections of the sensor port 422 considered pairwise. Sensing the impedance can be useful for detecting, among other things, whether the defibrillation electrodes 442, 444 and/or the sensing electrodes 424 are not making good electrical contact with the body of the patient 108. The patient physiological signals may be sensed when available. The measurement circuit 420 can then render or generate information about the sensed signals as inputs, data, other signals, etc. As such, the measurement circuit 420 can be configured to render a patient input responsive to a patient parameter sensed by a sensor. In some embodiments, the measurement circuit 420 can be configured to render a patient input, such as values of an ECG signal, responsive to the ECG signal sensed by the sensing electrodes 424. Specifically, the information rendered by the measurement circuit 420 is outputted, but the information can be called an input because this information is received as an input by a subsequent device or functionality.

The processor 404 may be implemented in several ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on. The processor 404 may include, or have access to, a non-transitory storage medium, such as memory 410. The memory 410 can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in the present disclosure.

Further, the processor 404 can be considered to have a number of modules. One such module can be the detection module 406. The detection module 406 can include a Ventricular Fibrillation (VF) detector. The patient's sensed ECG from the measurement circuit 420, which can be available as inputs, data that reflect values, or values of other signals, may be used by the VF detector to determine whether the patient 108 is experiencing VF. Detecting VF is useful because VF typically results in SCA. The detection module 406 can also include a Ventricular Tachycardia (VT) detector, and so on.

Another module in the processor 404 can be the advice module 408, which generates advice for what to do. The advice can be based on outputs of the detection module 406. There can be many types of advice according to embodiments. In some embodiments, the advice is a shock/no shock determination that the processor 404 can make, for example, via the advice module 408. The shock/no shock determination can be made by executing a stored shock advisory algorithm. The shock advisory algorithm can make a shock/no shock determination from one or more ECG signals that are captured according to the embodiments and determine whether or not a shock criterion is met. The determination can be made from a rhythm analysis of the captured ECG signal or otherwise.

In some embodiments, when the determination is to shock, an electrical charge is delivered to the patient 108. Delivering the electrical charge is also known as discharging and shocking the patient 108. As mentioned above, such can be delivered for defibrillation, pacing, and so on. In ideal conditions, a very reliable shock/no shock determination can be made from a segment of the sensed ECG signal of the patient 108. In practice, however, the ECG signal is often corrupted by electrical noise, which makes it difficult to analyze. Too much noise sometimes causes an incorrect detection of a heart arrhythmia, resulting in a false alarm to the patient 108. Noisy ECG signals may be handled as described in U.S. patent application Ser. No. 16/037,990, filed on Jul. 17, 2018 and published as US 2019/0030351 A1, and also in U.S. patent application Ser. No. 16/038,007, filed on Jul. 17, 2018 and published as US 2019/0030352 A1, both by the same applicant and incorporated herein by reference.

The connection verification module 110, as previously described in FIG. 1, has the function of monitoring the pairing of the wearable medical device 102 to the mobile communication device 104. In addition, if the internal monitoring device 416 is indeed provided, the processor 404 may receive inputs or parameters from the internal monitoring device 416.

The external defibrillator 400 may optionally further include the memory 410, which can operate together with the processor 404. The memory 410 may be implemented in a number of ways. Such ways include, by way of example and not of limitation, volatile memories, Non-volatile Memories (NVM), Read Only Memories (ROM), Random Access Memories (RAM), magnetic disk storage media, optical storage media, smart cards, flash memory devices, any combination of these, and so on. The memory 410 is thus a non-transitory storage medium. The memory 410, if provided, can include programs for the processor 404, which the processor 404 may be able to read and execute. More particularly, the programs can include sets of instructions in the form of code, which the processor 404 may be able to execute upon reading. The programs may also include other information such as configuration data, profiles, scheduling, and the like that can be acted upon by the instructions. Executing is performed by physical manipulations of physical quantities, and may result in functions, operations, processes, acts, actions and/or methods to be performed, and/or the processor 404 to cause other devices or components or blocks to perform such functions, operations, processes, acts, actions and/or methods. The programs can be operational for the inherent needs of the processor 404 and can also include protocols and ways that decisions can be made by the advice module 408. In addition, the memory 410 can store prompts for the patient (or user) 108 if the user 108 is a local rescuer. Moreover, the memory 410 can store data which may include but is not limited to the patient data, system data, and environmental data, as learned by the internal monitoring device 416. The patient data storage module 109 (not shown in FIG. 4), as described in previous figures, may store the patient data specifically in the memory 410. The data can be stored in the memory 410 before it is transmitted out of the external defibrillator 400, or be stored thereafter upon receipt by the external defibrillator 400.

The external defibrillator 400 can optionally include the communication module 412, for establishing one or more wired or wireless communication links with other devices of other entities, such as a remote assistance center, Emergency Medical Services (EMS), and the like. The communication links can be used to transfer data and commands. The data may be patient data, event information, therapy attempted, Cardiopulmonary Resuscitation (CPR) performance, system data, environmental data, and so on. For example, the communication module 412 may transmit wirelessly, e.g., on a daily basis, heart rate, respiratory rate, and other vital signs data to a server accessible over the internet, for instance as described in US 20140043149. The data can be analyzed directly by the physician and can also be analyzed automatically by algorithms designed to detect a developing illness and then notify medical personnel via text, email, phone, and other means of communication. The communication module 412 may also include such interconnected sub-components as may be deemed necessary by a person skilled in the art, for example an antenna, portions of the processor 404, supporting electronics, outlet for a telephone or a network cable, and the like.

The external defibrillator 400 may also include the power source 414. To enable portability of the external defibrillator 400, the power source 414 typically includes a battery. The battery is typically implemented as a battery pack, which can be rechargeable or not. Sometimes a combination is used of rechargeable and non-rechargeable battery packs. Other embodiments of the power source 414 can include an AC power override, for where AC power will be available, an energy-storing capacitor, and so on. Appropriate components may be included to provide for charging or replacing the power source 414. In some embodiments, the power source 414 is controlled and/or monitored by the processor 404.

The external defibrillator 400 may additionally include the energy storage module 430. The energy storage module 430 can be coupled to the support structure of the wearable medical device 102, for example either directly or via the electrodes and their leads. The energy storage module 430 can be configured to store some electrical energy temporarily in the form of an electrical charge, when preparing it for discharge to administer a shock. In some embodiments, the energy storage module 430 can be charged from the power source 414 to the desired amount of energy, as controlled by the processor 404. In some implementations, the energy storage module 430 includes the capacitor 428, which can be a single capacitor or a system of capacitors, and so on. In some embodiments, the energy storage module 430 includes a device that exhibits high power density, such as an ultracapacitor. As described above, the capacitor 428 can store the energy in the form of an electrical charge, for delivering to the patient 108.

A decision to shock can be made responsive to the shock criterion being met, as per the abovementioned determination. When the decision is to shock, the processor 404 can be configured to cause at least some or all of the electrical charge stored in the energy storage module 430 to be discharged through patient 108 while the support structure is worn by patient 108, so as to deliver a shock to the patient 108.

For causing the discharge, the external defibrillator 400 includes the discharge circuit 434. When the decision is to shock, the processor 404 can be configured to control the discharge circuit 434 to discharge through the patient 108 at least some of all of the electrical charge stored in the energy storage module 430. Discharging can be to the electrical nodes 436, 438, and subsequently to the defibrillation electrodes 442, 444, so as to cause a shock to be delivered to the patient 108, thereby facilitating therapy treatment. The discharge circuit 434 can include the one or more switches 432. The one or more switches 432 can be made in a number of ways, such as by an H-bridge, and so on. The discharge circuit 434 could also be thus controlled via the processor 404, and/or the user interface 116. A time waveform of the discharge may be controlled by thus controlling the discharge circuit 434. The amount of energy of the discharge can be controlled by how much the energy storage module 430 has been charged, and also by how long the discharge circuit 434 is controlled to remain open. The external defibrillator 400 can optionally include other components. Components of the mobile communication device 104 will now be described with respect to FIGS. 5 and 6.

An example operation of the variable interface module 112 included in the mobile communication device 104 is described in FIG. 5, according to embodiments of the present disclosure. Specifically, FIG. 5 illustrates an embodiment of an interactive survey such as survey 500 provided by the variable interface module 112, through which the patient 108 can customize the user interface 116 of the mobile communication device 104. As depicted in FIG. 5, six survey questions are provided or presented to the patient 108 (or user). The survey questions may be presented during the fitting process or during the setup of the medical system 100 to customize the user interface 116. However, the scope of the present disclosure is not limited to either the number of questions or the type of questions i.e., the number of questions and type of questions may vary for different users. Further, in certain embodiments, the survey 500 may implement a type of decision tree in which one answer/ response to a particular survey question may lead to a set of question(s), while a different answer to the particular survey question may lead to a different set of question(s) with a different number of questions. The exemplary questions depicted in the survey 500 may appear in a sequential order or may be randomly chosen and presented out of order to the patient 108, without limitation.

Referring to FIG. 5, exemplary six questions of the survey 500 pertain to screens 502, 504, 506, 508, 510, and 512 as presented to the patient 108 on the user interface 116 of the mobile communication device 104. Each of the screens depicted in FIG. 5 features a question to enable personalized customization of the user interface 116 for the patient 108. In particular, screens 502, 504, 506, 508, 510, and 512 indicate visual interface selections including a language selection, a mobile device usage level selection, a level of instruction detail selection, a button size selection, a font size selection, and a background color selection, respectively. The various selections related to different elements of the user interface 116 described herein may be referred to as "settings" of the user interface 116.

In an embodiment, initially, the user interface 116 on the mobile communication device 104 provides an option to the patient 108 for selecting a language from the set of languages (for example, English, Spanish, Japanese, and/or the like), as shown in screen 502. Subsequently, the patient 108 selects a suitable language from the screen 502 via the user interface 116 that receives the patient input. After selection of the language or independently as a survey question, the user interface 116 on the mobile communication device 104 allows the patient 108 to indicate a level of detail for the instructions to be displayed on the user interface 116. An exemplary question may be presented such as "On a scale from 1 to 5, how detailed would you like your instructions to be?" as indicated in screen 504. In some examples, as depicted in FIG. 5, the patient 108 may rate the instructions on a scale of 1 to 5 using numerical icons shown on the screen 504. The patient 108 may select an icon according to their level of comfort with technology or complexity of the user interface 116 on the mobile communication device 104. The selection of numerical icon on the screen 504 may further vary depending on patient demographics. An old-age patient, for example, may select numerical icon 5 as such a patient may not be comfortable with using the mobile communication device 104 and would require instructions on the user interface 116 to be as detailed as possible. A teenager patient, on the other hand, may select numerical icon 1 as such a patient may find the user interface 116 easy to comprehend and use, and may prefer straightforward and less detailed instructions.

After the patient 108 enters a response to the question on screen 504 or independently as a survey question, the user interface 116 on the mobile communication device 104 requests the patient 108 to select a statement from the set of statements on screen 506, which may relate to their previous experience with using smartphones or the mobile communication device 104. Although screen 504 uses the word "smartphone", however one may use the word "mobile communication device" consistently for screens 506, 510, and 512 without departing from the scope of the present disclosure. For example, the statements on screen 504 may include "I have never used a smartphone before", "I have used a smartphone before but would not say I am experienced with them", "I am somewhat comfortable using a smartphone", "I am very comfortable using a smartphone", and/or the like. The patient 108, based on their comfort with using smartphones, may select one out of four exemplary statements on screen 506 to record their response. In response to the selection on screen 506 or independently as a survey question, the user interface 116 on the mobile communication device 104 allows the patient 108 to select a button size on screen 508. Exemplary button sizes in increasing order of sizes are displayed as numerical icons 1 to 5 on screen 508. The patient 108 may select an appropriate button size according to their visual capability or eyesight to customize the user interface 116. As an example, a patient with diminished vision may select icon 5 to display buttons on the user interface 116 at a maximum size, while a patient with perfect vision may select icons 1 or 2 based on their display preference.

In response to the selection on screen 508 or independently as a survey question, the user interface 116 on the mobile communication device 104 allows the patient 108 to select a font size on screen 510. Exemplary five options with variable font size from minimum to maximum are presented on screen 510 for patient selection. The patient 108, based on their vision or visual capability, may select a suitable font size option among the presented options that is easily readable for different UI elements of the user interface 116. Similar to button size selection example, different patients may select different options based on their display preferences or visual appeal.

In response to the selection on screen 510 or independently as a survey question, the user interface 116 on the mobile communication device 104 allows the patient 108 to select a background color on screen 512 for displaying information. In some examples, the background color selection options may include yellow, green, blue, orange, purple, and/or the like. Such specific question on screen 512 enables patients with color blindness or color vision deficiency (CVD) to make an appropriate selection that suits their display needs. In an alternate embodiment, instead of background color, the survey question may include asking whether the patient 108 would like to use an image as background on the user interface 116. Based on patient's response, the background may be set as the image selected by the patient 108, which may further enhance patient engagement with the mobile communication device 104 due to the personalized background being set up.

Apart from the survey questions depicted in FIG. 5, as another survey question, the user interface 116 on the mobile communication device 104 may ask the patient 108 if the user interface 116 needs to be optimized for bright conditions during daytime and low light conditions during evenings or nighttime. In response to the patient's reply, the user interface 116 may adjust the UI elements for the patient 108 based on daytime and nighttime conditions. The optimization of the user interface 116 would help in saving battery consumption of the mobile communication device 104.

As yet another survey question, the user interface 116 may present a question asking whether the patient 108 would like to receive an audible and/or tactile indication in response to selection of a UI button/element by the patient 108. As a non-limiting example, the application running on the mobile communication device 104 or the user interface 116 may present a survey question and the patient 108, in response to the survey question, may select a "yes" or "no" soft button on the user interface 116. In response to the selection of "yes" button, for example, the application or user interface 116 may output "you pressed YES" and transmit a haptic feedback when the patient 108 presses the button to make a selection. In order to capture patient's feedback, the survey question, as a follow-up question, may include asking the patient 108 if the patient 108 likes the audible and/or tactile indication presented by the user interface 116. The patient's response can be looped in to adjust or re-adjust configuration of UI elements to provide a user-friendly and more engaging experience to the patient 108.

Further, the application running on the mobile communication device 104 or the user interface 116 may present additional questions to the patient 108 pertaining to patient's particulars (e.g., patient's name, surname, birthplace, spouse, friends, family etc.), career, hobbies, pets, and the like. The application may capture patient's responses to the additional questions that may be used to generate prompts for one or more patient engagement features such as jokes or riddles. The prompts for the patient 108 may be generated using built-in intelligence of the application or using an AI-based virtual assistant that functions considering the contextual information of the user 108 or patient 108, which includes the patient's responses to the additional questions.

In certain embodiments, the patient 108 can respond to the questions on the survey 500 about the user interface 116, and the variable interface module 112 can store and/or process the responses for adjusting or altering various visual elements of the user interface 116. The variable interface module 112 reconfigures the user interface 116 according to the survey responses and may present previews of the reconfigured user interface to the patient 108. The patient 108 may have an option to accept or decline the reconfiguration of the user interface 116, in some embodiments.

In certain embodiments, the mobile communication device 104 may interact with the patient 108 by changing the user interface 116 based on the detection of less patient usage or poor engagement of the patient 108 with the wearable medical device 102. This aspect of dynamically changing or customizing the user interface 116 by the mobile communication device 104 may encourage the patient 108 to increase the usage of the mobile communication device 104.

Further, in some embodiments, the mobile communication device 104 may update one or more settings of the user interface 116 to increase communication between the wearable medical device 102, the mobile communication device 104, and the remote server 106 when an interaction threshold is exceeded. The interaction threshold may refer to a minimum amount of time when the patient 108 is not interacting with the mobile communication device 104 (or the application running on the mobile communication device 104). For example, the interaction threshold may be set between 4 hours to 24 hours. Once the interaction threshold is exceeded, the mobile communication device 104 may update one or more settings of the user interface 116 automatically to increase communication of the patient 108 with the mobile communication device 104.

Although the embodiment of FIG. 5 discloses visual interfaces for displaying the survey questions in survey 500, however, in other embodiments, the patient 108 may have an option to select an audio interface for the survey 500. In such embodiments, the user interface 116 provides the survey questions audibly using a speaker of the user interface 116, the responses are received and stored via a microphone of the user interface 116. Additionally, or alternatively, the technology may be used by a Patient Service Representative (PSR) rather than the patient 108 themselves. In some embodiments, the mobile communication device 104 can read the survey 500 to the patient 108 in case the patient 108 has difficulty with eyesight or suffers from manual dexterity. In some embodiments, the mobile communication device 104 can be configured to re-deliver the survey 500 to update the responses if the mobile communication device 104 detects one or more of changes in historical patterns of usage or non-usage of the mobile communication device 104, errors in using the mobile communication device 104, deletion and saving of outputs provided to the patient 108 by the mobile communication device 104.

Therefore, in accordance with the embodiments described herein, the mobile communication device 104 may be configured with a functionality to present the survey-based variable UI designed to optimize the UI to the patient's needs and technology background. In some embodiments, the functionality may be provided in an application that may be installed/downloaded and run on the mobile communication device 104. For example, the application may be ASSURE® patient application, specifically named as ASSURABILITY, offered by Kestra Medical Technologies, Inc. of Kirkland, Washington that is installed on the mobile communication device 104 which is provided as part of ASSURE® system offering by same firm. The ASSURE® system including ASSURE® WCD may be implemented as the medical system 100 and the wearable medical device 102, respectively.

As discussed previously, the patient engagement module 114 may provide the feature of "heart rewards" via the patient application (e.g., ASSURE® patient application named ASSURABILITY), where the feature allows the patients 108 to earn different hearts based on the amount of time per day the wearable medical device 102 is worn by the respective patients 108. The "heart rewards" feature is exemplified in FIG. 6.

Figure 6:
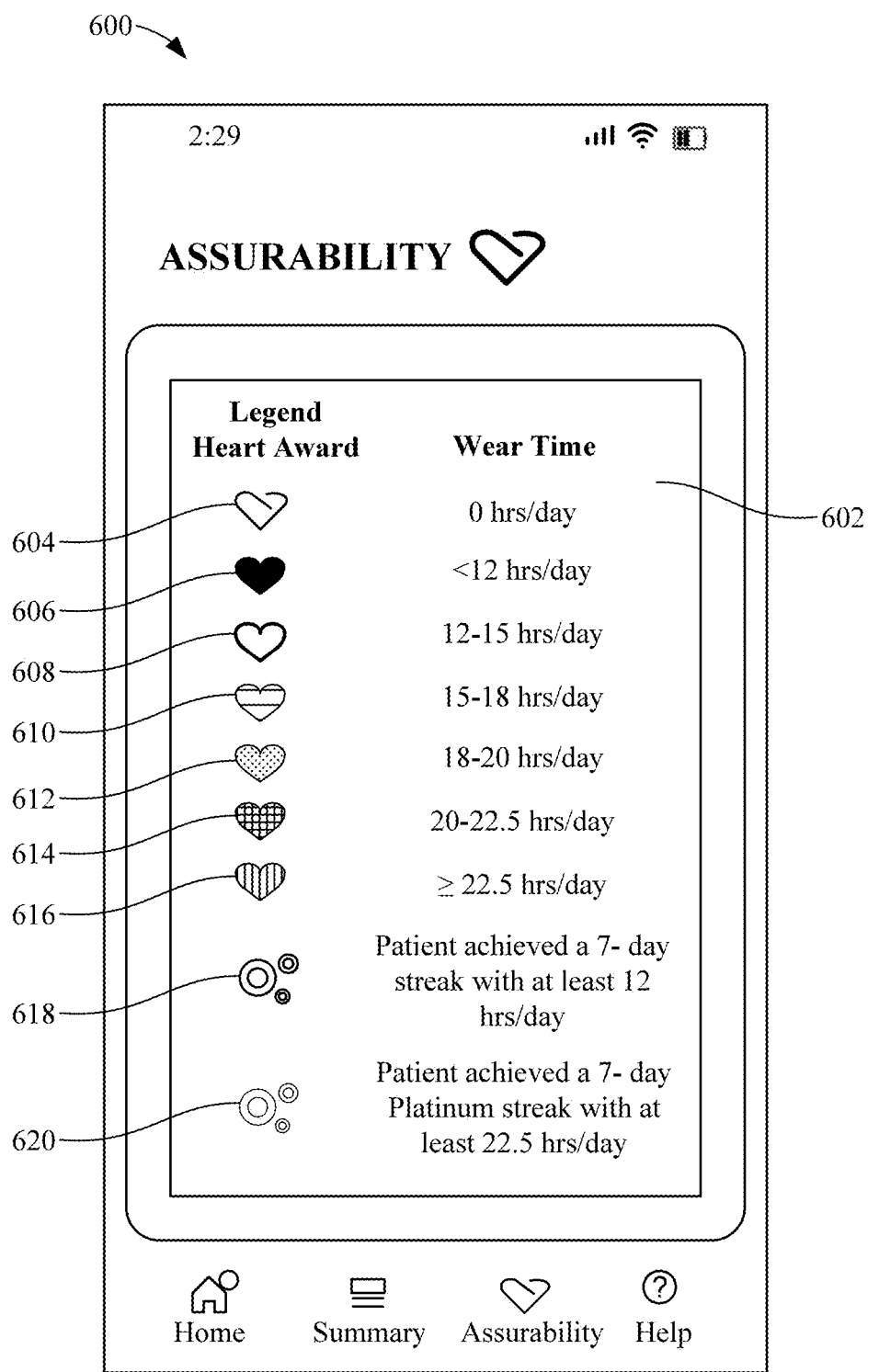
FIG. 6 illustrates different heart award legends and corresponding wear times of the wearable medical device, according to an embodiment of the present disclosure.

FIG. 6 illustrates different heart award legends and corresponding wear times of the wearable medical device 102 on a user interface 600 of the mobile communication device 104. The user interface 600 is presented by ASSURABILITY or ASSURE® patient application which is a part of the ASSURE® system. As depicted in FIG. 6, screen portion 602 displays seven heart symbols, two streak symbols, and corresponding wear times per day for the wearable medical device 102. The corresponding wear times per day (or total time for which the wearable medical device 102 is being worn) are tracked for each patient 108 between 12:00 am and 11:59 pm on any given day.

For example, various heart symbols include a first heart symbol 604, which depicts that the patient 108 has not worn their ASSURE® system or WCD that day, accounting for 0 hours wear time. As a non-limiting example, the first heart symbol 604 may be color coded as hollow black heart. A second heart symbol 606 depicts that the patient 108 has worn their ASSURE® system or WCD for less than 12 hours per day. As a non-limiting example, the second heart symbol 606 may be color coded as a black heart. A third heart symbol 608 depicts that the patient 108 has worn their ASSURE® system or WCD between 12 to 15 hours per day. As a non-limiting example, the third heart symbol 608 may be color coded as a red heart. A fourth heart symbol 610 depicts that the patient 108 has worn their ASSURE® system or WCD between 15 to 18 hours per day. As a non-limiting example, the fourth heart symbol 610 may be color coded as a bronze heart. A fifth heart symbol 612 depicts that the patient 108 has worn their ASSURE® system or WCD between 18 to 20 hours per day. As a non-limiting example, the fifth heart symbol 612 may be color coded as a silver heart. A sixth heart symbol 614 depicts that the patient 108 has worn their ASSURE® system or WCD between 20 to 22.5 hours per day. As a non-limiting example, the sixth heart symbol 614 may be color coded as a gold heart. A seventh heart symbol 616 depicts that the patient 108 has worn their ASSURE® system or WCD for at least 22.5 hours per day. As a non-limiting example, the seventh heart symbol 616 may be color coded as a platinum heart. Further, a first streak symbol 618 may correspond to colored stars if the patient 108 achieves a 7-day streak with at least 12 hours per day of wear time per day. The patient 108 may be presented with purple stars, for example, as the first streak symbol 618 to show 7-day streak. Furthermore, a second streak symbol 620 may correspond to different colored stars if the patient 108 achieves a 7-day platinum streak with at least 22.5 hours of wear time per day. The patient 108 may be presented with blue stars, for example, as the second streak symbol 620 to show 7-day platinum streak.

The various symbols exhibited in FIG. 6 are meant to help the patients 108 understand the color-coding of the heart awards on their individual UI of the patient application and on a national patient leaderboard, described later in FIG. 8. Besides improving engagement of the patient 108 with the patient application, the heart awards feature motivates the patients 108 to wear the ASSURE® system or WCD for more time in order to earn better heart rewards for consecutive wear days. In addition or as an alternative to the heart awards earned by the patients 108, the patient engagement module 114 may present the patients 108 with different compliance status tiers that are assigned to each patient 108 based on their respective wear times of the wearable medical device 102 (or WCD wear times). Details regarding the compliance status tiers are explained in FIG. 7.

Figure 7:
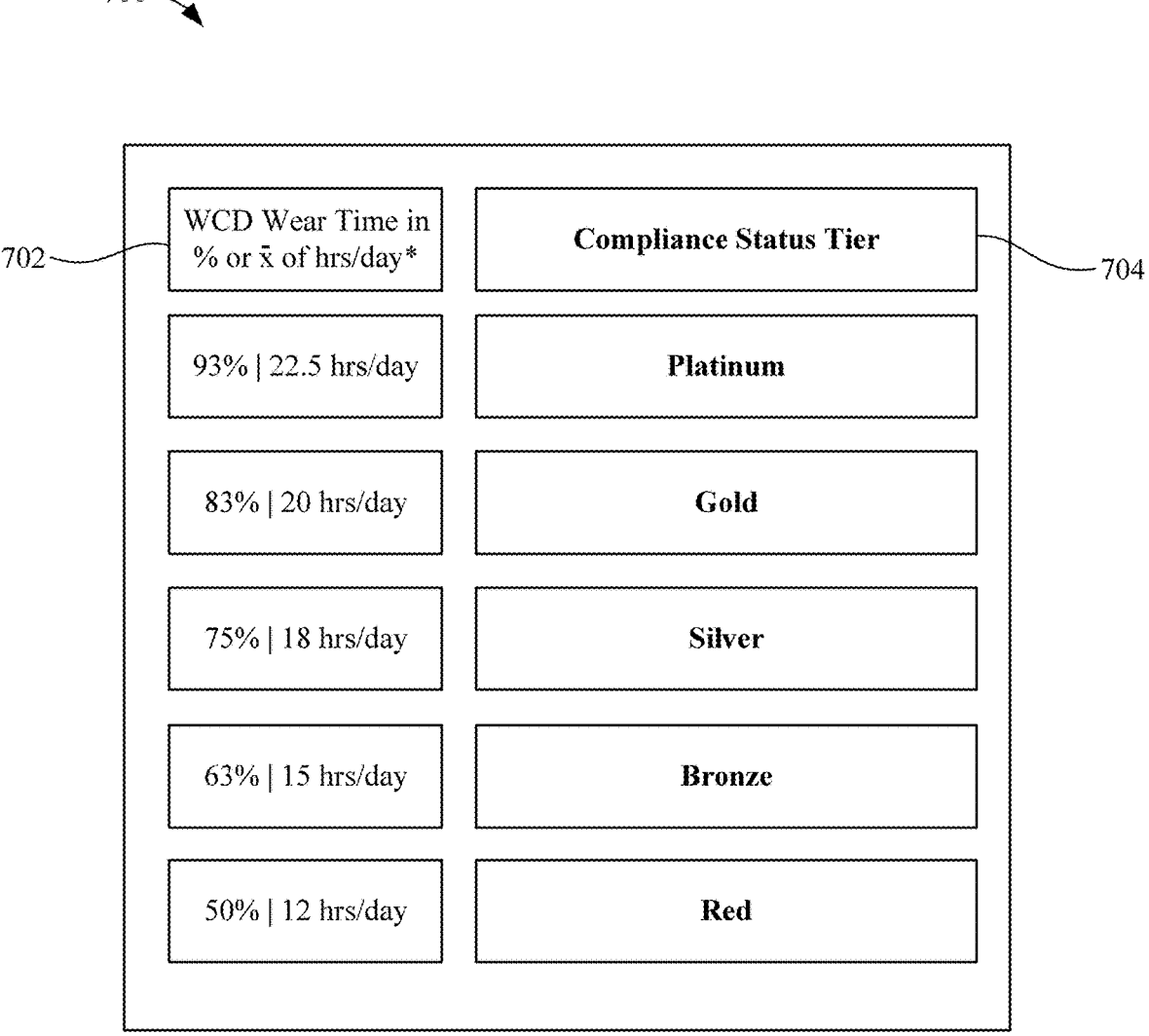
FIG. 7 illustrates compliance status tiers corresponding to wear times of the wearable medical device, according to an embodiment of the present disclosure.

FIG. 7 illustrates a user interface 700, presented by the ASSURABILITY or ASSURE® patient application, that displays various compliance status tiers corresponding to the wear times of the wearable medical device 102. Specifically, FIG. 7 displays WCD wear time 702 of the patient 108 in percentages or as number of hours per day when the wearable medical device 102 is being worn. Patients 108 receive a compliance status tier 704 based on their overall WCD wear time 702 since they began wearing their ASSURE® system. The data used to calculate the individual compliance status tier excludes the first day, last day, and any days the wearable medical device 102 was not worn at all by the patient 108.

The compliance status tier 704 ranges from the lowest tier "red" to the highest tier "platinum" that the patient 108 may earn. To earn the "Red" compliance status, the patient 108 must be wearing their wearable medical device 102 for at least 50% of the total time they have had their ASSURE® system, or 12 hours per day. To earn the "Bronze" compliance status, the patient 108 must be wearing their wearable medical device 102 for at least 63% of the total time they have had their ASSURE® system, or 15 hours per day. To earn the "Silver" compliance status, the patient 108 must be wearing their wearable medical device 102 for at least 75% of the total time they have had their ASSURE® system, or 18 hours per day. To earn the "Gold" compliance status, the patient 108 must be wearing their wearable medical device 102 for at least 83% of the total time they have had their ASSURE® system, or 20 hours per day. To earn the "Platinum" compliance status, the patient 108 must be wearing their wearable medical device 102 for at least 93% of the total time they have had their ASSURE® system, or 22.5 hours per day. The information pertaining to compliance status tiers for respective patients 108 may be seen on the individual UI on rewards tab of the patient application and on their Kestra CareStation® Report, which will be described in subsequent figures.

Figure 8:
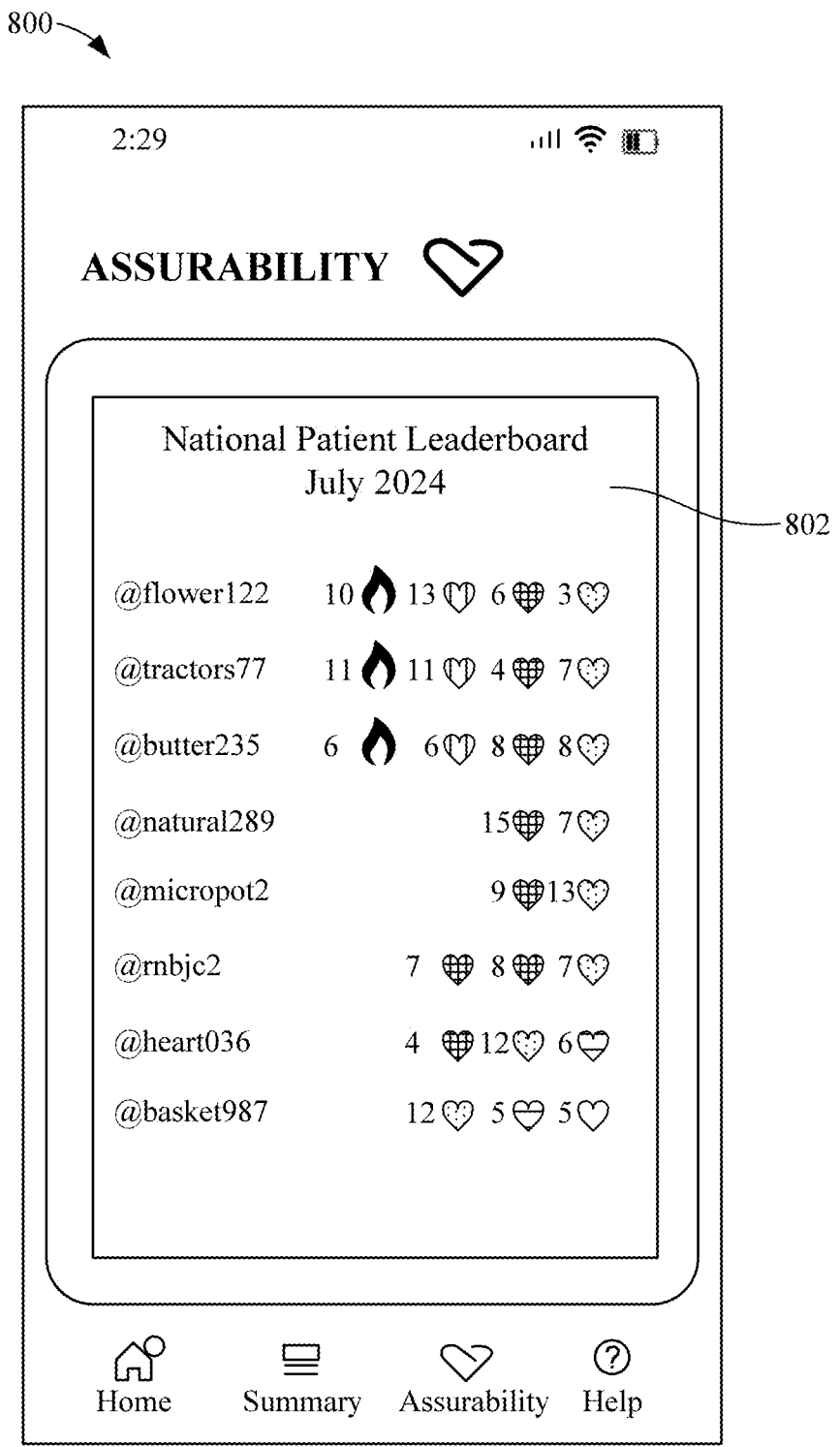
FIG. 8 illustrates a national patient leaderboard, according to an embodiment of the present disclosure.

FIG. 8 illustrates a user interface 800 displaying a national patient leaderboard 802 for a particular month and year (e.g., July 2024). FIG. 8 is described in conjunction with previous figures. The national patient leaderboard 802 is an interactive feature, offered by the patient engagement module 114 and presented by the patient application, for patients 108 to compare their wear time of the respective wearable medical devices 102 with other patients nationally. In specific embodiments, the patients 108 may be linked to each other via ASSURE® system or WCDs that they use or wear. However, without limitation, a pool of patients for the national patient leaderboard 802 may be aggregated based on geography, medical centers, WCD type, health condition type, current health status, and/or the like. The purpose of the national patient leaderboard 802 is to bring an element of competition among the patients 108 to encourage wear time and compliance. Different symbols may be used to depict heart awards and streaks, similar to those described in FIG. 6. As a non-limiting example, a fire symbol or emoticon may be used to identify patients having platinum streaks.

In FIG. 8, various usernames (e.g., @name) corresponding to different patients with their earned heart awards and/or streaks are shown. For the national patient leaderboard 802, patients 108 are given usernames to protect their personal health information. For example, a patient with username as @flower122 in FIG. 8 has a platinum streak of 10 days. The numbers displayed next to the symbols represent the number of days for streaks or heart awards. Therefore, the national patient leaderboard 802 facilitates healthy competition among the pool of patients and encourages each individual patient 108 to earn better heart awards and create streaks by consistently wearing the respective WCDs or wearable medical devices 102 over a period of time.

Figure 9:
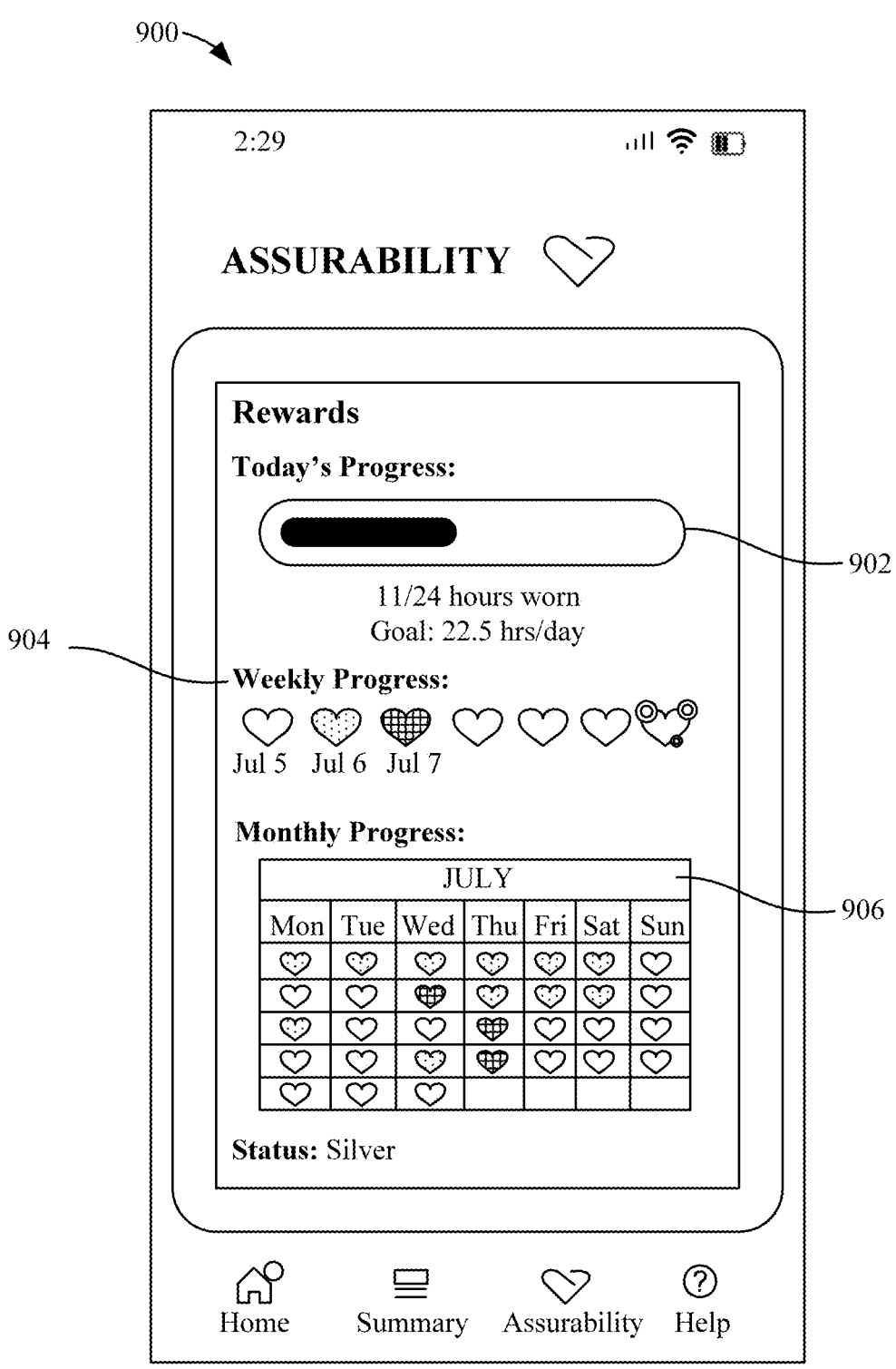
FIG. 9 illustrates a user interface exhibiting heart award progress of a patient, according to an embodiment of the present disclosure.

FIG. 9 illustrates a user interface 900 exhibiting heart award progress of a patient. The user interface 900 may correspond to rewards page or tab on the ASSURE® patient application. Specifically, the user interface 900 depicting patient's individual heart awards progress includes daily progress 902, weekly progress 904, and monthly progress 906.

In daily or today's progress 902, a patient can view a progress bar with their daily goal and their progress towards meeting that goal. For example, under the depicted daily progress 902, a particular patient (e.g, patient 108) wore their WCD (e.g., wearable medical device 102) for 11 hours in a 24-hour period against the recommended wear time or goal of 22.5 hours per day. Such presentation of statistics on the user interface 900 may enable patients to inch towards their daily goal by regular monitoring of the progress bar and comparison between the actual wear time and the goal in real time. The progress bar may change colors, for example from red to silver, once the patient reaches that level for the day. In certain embodiments, the color scheme for progress bar of the daily progress 902 may correspond to color scheme for heart awards.

For weekly progress 904, a patient may see seven empty hollow hearts of a specific color (e.g., gray) at the beginning of the week, and after each 24-hour period is complete, the heart symbols may be filled in with the color that corresponds to the wear time they achieved. The heart symbol, in some embodiments, may also be labeled with the date held for easy correspondence between the date versus heart award. A hollow heart symbol of a specific color (e.g., black) with a number is indicative of the day that they are currently on, and the heart symbol will be filled in after the day is complete. To further motivate the patients 108, a star symbol of a specific color (e.g., purple) on the seventh day may appear with an animation if they achieve a 7-day wear time streak with at least 12 hours of wear time per day, as an example.

For monthly progress 906, the patients 108 may see their heart awards fill in their monthly calendar as and when they are achieved. If a patient achieves a week, or 7 days, of platinum heart awards, then they may receive the coveted blue sparkles, serving as a badge of honor for a particular patient for achieving the feat of recommended wear time per day for an extended duration.

Further, the user interface 900 may display patient's compliance status tier, which corresponds to overall wear time, at the bottom of the screen. Therefore, the user interface 900 presents a summarized snapshot of an individual patient's progress on a single interface, thereby allowing the individual to track, maintain, and/or improve their wear time and earn better compliance status tier.

FIG. 10 illustrates exemplary notifications 1000 from an application (e.g., ASSURABILITY or ASSURE® patient application) based on the wear times of the wearable medical device 102 by the patient 108. In some embodiments, the ASSURABILITY application may send push notifications to the patient 108 to keep them working towards their goals, congratulate them for their consistent wear, and remind them to continue wearing their wearable medical device 102 (e.g., WCD) for at least 22.5 hours per day, as an example.

Specifically, a first notification 1002 displays an example notification that a particular patient would receive if they wore their WCD for the full recommended time (at least 22.5 hours/day), congratulating the particular patient, and reminding them of why it's important to wear the WCD for the full recommended time. A second notification 1004 is an example notification that a particular patient would receive if they did not wear the WCD for the full recommended time, notifying them of their wear time, and reminding them that the WCD should be worn any time the particular patient is not showering, bathing, or swimming. The second notification 1004 also includes a helpline phone number (e.g., ASSURE® helpline) for patient's reference, in case their shorter wear time was due to any issues with their WCD. A third notification 1006 is an example notification that a particular patient would receive if they achieved a platinum streak, notifying them of their status on the national patient leaderboard 802 and encouraging them to keep up their good work on wear time compliance.

FIG. 11 illustrates an exemplary report 1100 depicting compliance status and other statistics of a patient. As described previously, Kestra CareStation® may be employed as the remote monitoring platform that service provider (e.g., Kestra) and physicians have access to, and where patient's heart trends, steps, usage, and episodes can be checked. The report 1100 pertaining to patient's compliance status may be displayed on an exported or printed CareStation® report.

Specifically, in FIG. 11, summary report 1102 identifies a wearable medical device (e.g., ASSURE® WCD) of a particular patient, and depicts patient data such as date of birth, medical record ID, patient's phone number, patient's clinic, patient's physician, and details pertaining to Kestra CareStation® username, report creation date, along with compliance status (e.g., indicated as Platinum). Further, WCD settings 1104 indicate a status of therapy (on or off) along with VT/VF indicators associated with the particular patient. Episodes 1106 indicate a status of various cardiac episodes (e.g., tachycardia, bradycardia/asystole, supraventricular tachycardia (SVT), and/or the like) that are experienced by the particular patient over a period of time. An indication of patient-triggered episodes are also included in the episodes 1106 that may be referred by physicians/doctors for treatment. Usage summary 1108 displays usage statistics of the WCD by the particular patient. The usage statistics may include but are not limited to last transmission date/time, number of active days, average per day, and number of hours the WCD is worn by the particular patient. Summary 1110 includes graphical representation of heart rate 1112, steps 1114, and usage 1116 of the particular patient over a predetermined period of time. Heart rate 1112 depicts median heart rate for day and night for the predetermined period of time. Steps 1114 depict daily average number of steps for the particular patient along with a demarcated steps target. As a non-limited example, steps 1114 depicts 2760 average steps against 1500 target number of steps for the particular patient. Usage 1116 depicts daily average time of using the WCD by the particular patient against a demarcated usage target. As a non-limited example, usage 1116 depicts 21:27 average time against 20:00 target usage for the particular patient.

The statistics displayed in the summary report 1102 and/or the summary 1110 may be utilized by doctors, physicians, clinicians, and/or authorized medical personnel to treat the underlying cardiac condition(s) of the patients 108. The treatment may include determinations for providing or not providing therapy to the respective patients 108 and/or changing the WCD settings 1104.

In addition to the patient engagement features discussed in the various embodiments, the patient engagement module 114 may be configured to provide features including appointment calendar, log book, connection invites, heart awards for recovery, monetary incentives, and/or the like. By provisioning the feature of appointment calendar, patient(s) 108 may add important dates on their calendar such as upcoming procedures and cardiology appointments. By accessing such data from the appointment calendar, CareStation® reports may be strategically delivered to patient's cardiologists before their next appointment. Further, patients 108 may create a checklist, write notes, or create logs to keep track of their medications, diet, and exercise. Patients 108 may also be rewarded with stars or awards for achieving their daily step goal. The feature of connection invites may enable the patient(s) 108 to connect with their family and friends. Specifically, the patient(s) 108 may invite their loved ones or family members to participate in their recovery. Invited members may be able to see heart rewards, WCD hours worn, steps, and notifications of a heart alert associated with the respective patient 108. Additionally, in order to motivate those patients who are recovering from drug or alcohol addiction or substance abuse, heart awards may be provided. The heart awards to such patients may serve as an indication to prove to their doctor that they are serious about their healthcare moving forward and are willing to be compliant. Moreover, monetary awards may be earned by patient(s) 108 in addition to the heart awards when a patient achieves a silver, gold, or platinum status. In an example, the monetary award may be reimbursement or relief from paying their insurance copay for patient(s) that do not have 100% insurance coverage.

Figure 12:
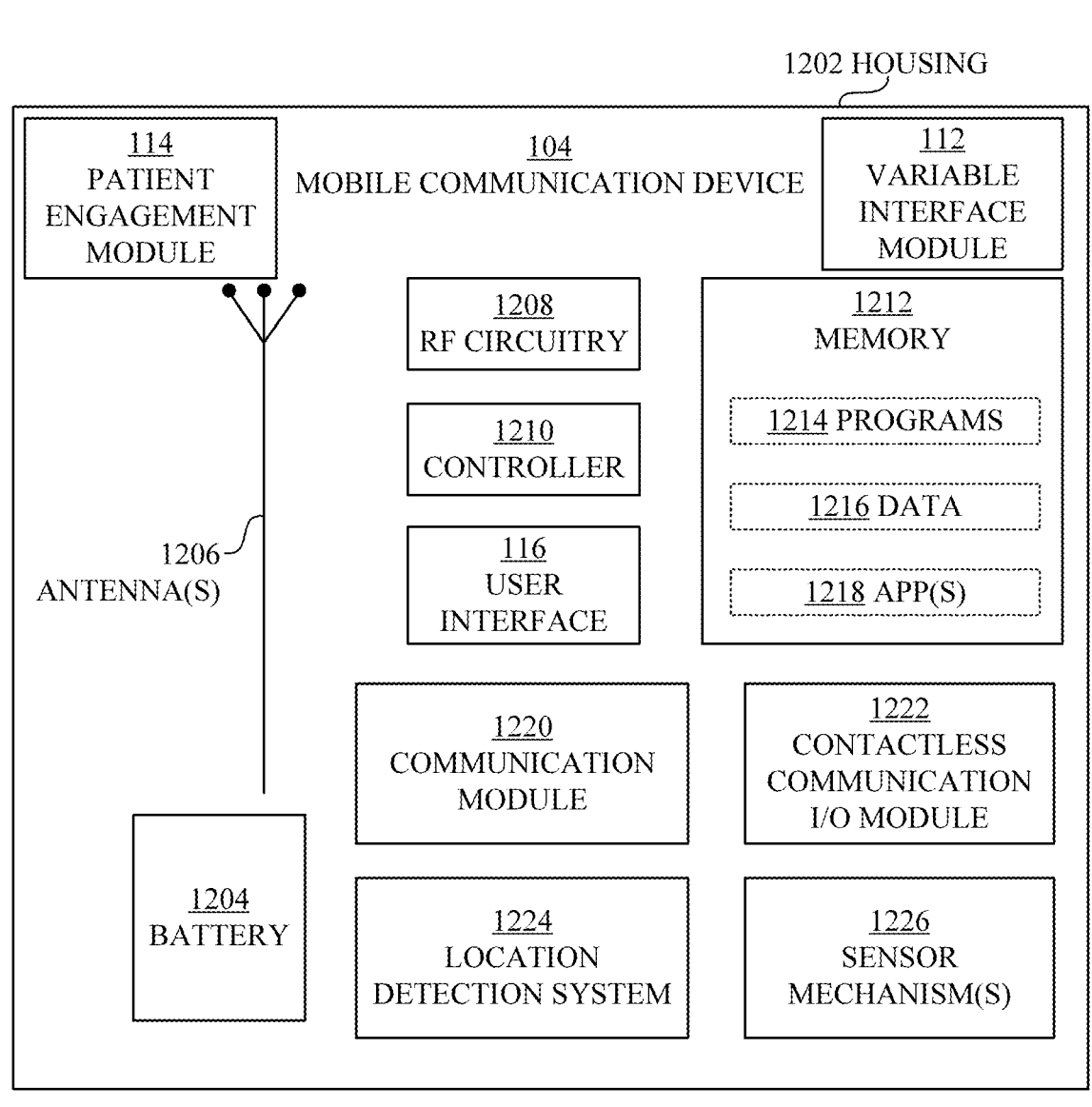
FIG. 12 illustrates a block diagram of the mobile communication device, according to an embodiment of the present disclosure.

FIG. 12 illustrates a block diagram 1200 showing exemplary components of the mobile communication device 104, according to an embodiment of the present disclosure. FIG. 12 is described in conjunction with previous figures. The mobile communication device 104, as shown in FIG. 12, is provided with a housing 1202, and the components of the mobile communication device 104 are housed within the housing 1202. The mobile communication device 104 is powered by a battery 1204 that is rechargeable, for portability of the mobile communication device 104.

The mobile communication device 104 includes one or more antennas 1206 for wireless communication. The mobile communication device 104 also includes Radio Frequency (RF) circuitry 1208. RF circuitry 1208 cooperates with antenna(s) 1206 to receive and send RF signals. RF circuitry 1208 is configured to convert wired electrical signals to/from RF signals. RF circuitry 1208 may include well-known circuitry for performing these functions, including but not limited to an RF transceiver, one or more amplifiers, a tuner, one or more oscillators, a digital signal processor, a Coder-Decoder (CODEC) chipset, a Subscriber Identity Module (SIM) card, a memory, and so forth. The one or more antennas 1206 and RF circuitry 1208 can establish communication links, when cooperating with one of the communication modules of the mobile communication device 104 that are described herein.

The mobile communication device 104 additionally includes a controller 1210, for controlling its operation. Controller 1210 can be one or more processors, implemented as a Central Processing Unit (CPU), a digital signal processor, a microprocessor, a microcontroller, an application specific Integrated circuit (ASIC), a programmable logic device (PLD) or other implementation. Controller 1210 can be optionally combined in a single chip with a memory controller and a peripherals interface.

Further, the mobile communication device 104 also includes a memory 1212, which can include both persistent/non-volatile and non-persistent/volatile memory components. Memory 1212 can be implemented in any technology for memory for such devices, for example RAM, ROM, Electrically Erasable Programmable Read-only Memory (EEPROM), flash memory, and so on. In some embodiments, additional memory components may be plugged in from a device external to the housing 1202, such as a thumb drive. As such, memory 1212 can include a non-transitory computer-readable storage medium. Memory 1212 can store programs 1214 and data 1216. Programs 1214 can include instructions that can be executed by the controller 1210. Programs 1214 may include an operating system, such as, for example, Android, iPhone Operating System (IOS), Windows, Symbian, or BlackBerry OS.

In addition, one or more applications (apps) 1218 can be stored in the memory 1212. App(s) 1218 can also include instructions that can be executed by the controller 1210. Common app(s) 1218 can be provided for a contacts module, an email client module, a calendar module, a camera module, a maps module, and the like.

It will be appreciated that many of the methods of the present disclosure can be performed by the mobile communication device 104 due to one or more special app(s) 1218, in addition to common app(s) 1218. Even if the mobile communication device 104 is initially provided in a more generic form without special app(s) 1218, the latter may be downloaded later.

Further, the mobile communication device 104 includes the user interface 116, as previously described with respect to FIG. 1. The user interface 116 may include individual devices for receiving inputs by the patient 108, generating outputs for the user 108, or both. The outputs for the patient 108 can be HPIs, such as but not limited to sounds, vibrations, lights, and images. Examples of such individual devices include a screen that could be a touch screen, a physical keypad, an optical finger interface, one or more speakers, one or more microphones, one or more accelerometers, and so on. Such devices can be included within the housing 1202, or can be added by a separate plugin, such as a keypad, a keyboard, a display, and a speaker. It should be noted that the user interface 116 is defined in a way such that it is displayed on a screen or a display, and hence the display may be regarded as a part of the user interface 116 and is not shown separately as a block in FIG. 12. In the various embodiments of the present disclosure, the display of the mobile communication device 104 may be operable to display the user interface 116.

Moreover, the mobile communication device 104 includes a communication module 1220. The communication module 1220 can conduct communication using any one of a variety of standards, protocols, and technologies. Examples of the technology include Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VOIP), Wi-MAX, a protocol for email (e.g., Internet Message Access Protocol (IMAP) and/or Post Office Protocol (POP)), instant messaging (e.g., Extensible Messaging and Presence Protocol (XMPP), Session Initiation Protocol for Instant Messaging and Presence Leveraging Extensions (SIMPLE), Instant Messaging and Presence Service (IMPS), and/or Short Message Service (SMS), or any other suitable communication protocol. Additionally, the mobile communication device 104 can include a contactless communication I/O module 1222. The contactless communication I/O module 1222 can be used for short range detection and communication, such as Near-Field Communications (NFC), Radio-frequency Identification (RFID), and the like.

The mobile communication device 104 can also include a location detection system 1224, which can be implemented with GPS. The mobile communication device 104 can further include one or more sensor mechanisms 1226. The sensor mechanism(s) 1226 can include one or more accelerometers, a proximity sensor, a magnetometer, optical sensors, an image sensor, and so on. Data captured by the location detection system 1224 and sensor mechanism(s) 1226 can be stored as data 1216.

Additionally, the mobile communication device 104 can include the variable interface module 112, the functionality of which is described above with respect to FIG. 1. Embodiments of the variable interface module 112, including an example operation as described above with respect to FIG. 5, can be used to modify the user interface 116 of the mobile communication device 104 in response to the survey 500 of the patient 108. The mobile communication device 104 can also include the patient engagement module 114, the functionality of which is also described above with respect to FIG. 1. The patient engagement module 114 may be utilized to enable the mobile communication device 104 to provide features to encourage patient engagement with the mobile communication device 104.

Programs 1214 and app(s) 1218 can advantageously coordinate their use with the components of the mobile communication device 104. For example, depending on the app(s) 1218, antenna(s) 1206 may be used to detect electromagnetic fields (EMF), and a microphone of the user interface 116 may be used to detect sound. Many of the components of the mobile communication device 104 are well known in the field, and therefore are not described further.

It will be appreciated that modes of the mobile communication device 104 can be used advantageously according to embodiments. For example, the mobile communication device 104 could be placed in a video mode for transmitting video in addition to transmitting voice as a telephone. Moreover, the mobile communication device 104 could be placed in an answer mode, so someone from the remote server 106 could talk with and listen to a bystander, without requiring the patient 108 to answer the call.

Figure 13:
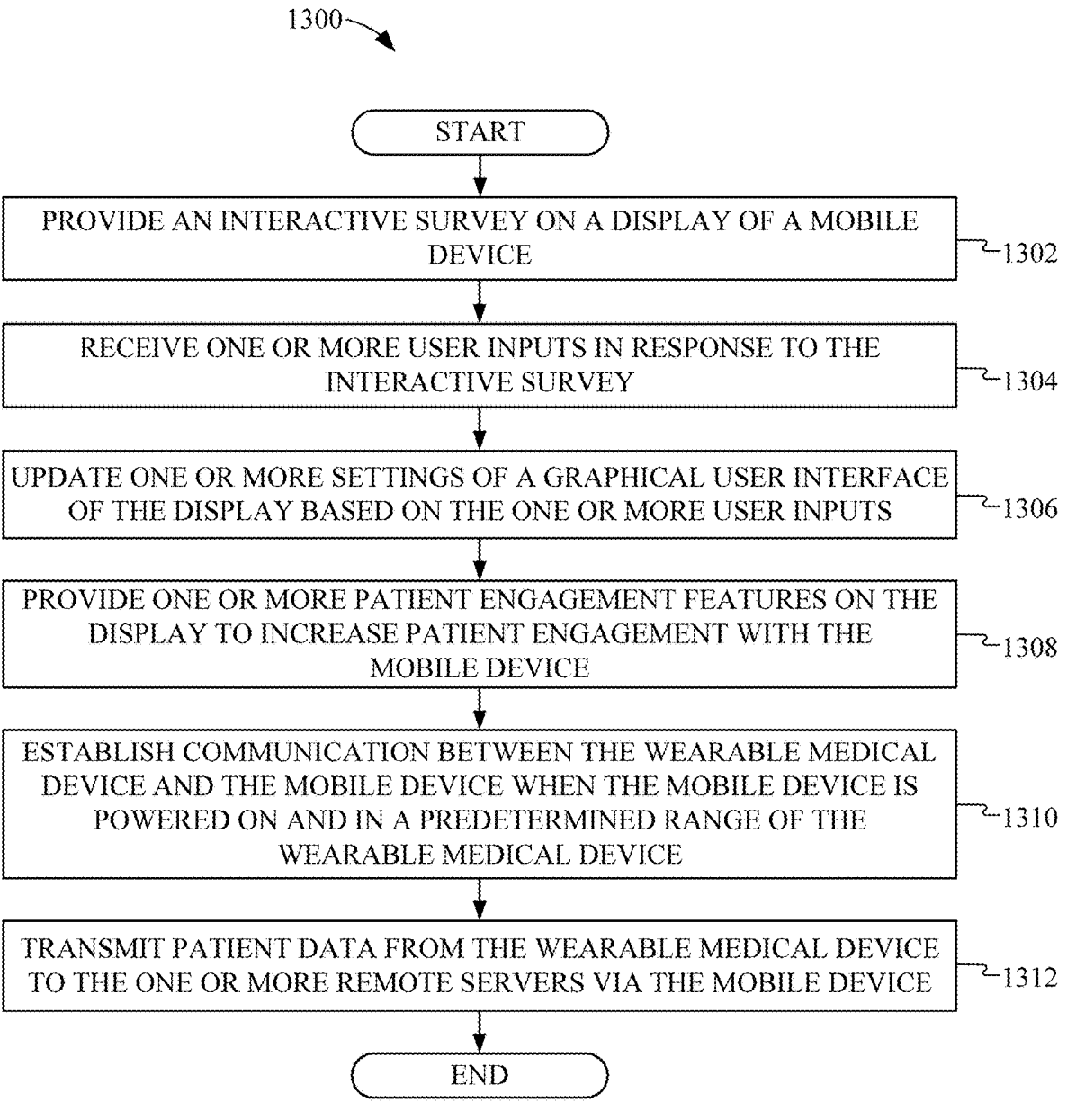
FIG. 13 illustrates an example method for transmitting patient data between the wearable medical device worn by the patient and one or more remote servers, according to an embodiment of the present disclosure.

FIG. 13 illustrates an example method 1300 for transmitting patient data between the wearable medical device 102 worn by the patient 108 and the remote server 106, according to an embodiment of the present disclosure. Method 1300 will be explained in conjunction with the previous figures. Although the example utilized for the method 1300 depicts a particular sequence of operations, the sequence may be altered without departing from the scope of the present disclosure. For example, some of the operations depicted may be performed in parallel or in a different sequence that does not materially affect the function of the method 1300. In other examples, different components of an example apparatus or system that implements the method 1300 may perform functions at substantially the same time or in a specific sequence.

In certain embodiments, as a pre-requisite requirement for transmitting the patient data, a dedicated smartphone or (personal) mobile communication device 104 for relaying the patient data to the remote server 106. As described previously, the mobile communication device 104 may be configured with the functionality to present the survey-based variable UI or the functionality may be provided in an application (e.g., ASSURE® patient application) as part of a medical system (e.g., ASSURE® system) that may be installed/downloaded and run on the patient's personal smartphone or the mobile communication device 104. However, other applications, medical systems, and wearable medical devices may be utilized without departing from the scope of the present disclosure. The UI or the application running on the mobile communication device 104 may include visual elements, audio elements, tactile elements, or a combination thereof for the patient 108 or any person using the application or mobile communication device 104, to facilitate interaction or communication with the patient 108 or user 108. Further, the application may automatically transmit the patient data at certain intervals or when the patient 108 chooses to transmit via the application. Without limitation, the mobile communication device 104 may be associated with the patient 108, the user 108, a family member or someone known to the patient 108, a rescuer, a trained caregiver, or any observer in the vicinity of the patient 108.

The method 1300 begins at block 1302 by providing an interactive survey on a display of a mobile device. In embodiments, the mobile communication device 104 provides the survey 500, as described above in FIG. 5, on the display of the mobile communication device 104 to receive one or more inputs from the patient 108 or user 108, as the case maybe. The survey 500 may include one or more audio interface selections and/or one or more visual interface selections including one or more of a language selection, a mobile device usage level selection, a level of instruction detail selection, a button size selection, a font size selection, and a background color selection. The examples of the language, level of instruction detail selection, mobile device usage level selection, button size selection, font size selection, and background color selection are presented on screens 502, 504, 506, 508, 510, and 512 respectively, as described in conjunction with FIG. 5.

The method 1300 further includes receiving one or more user inputs in response to the interactive survey, at block 1304. In embodiments, the mobile communication device 104 includes the user interface 116, which is described in conjunction with FIGS. 4 and 6. The user interface 116 includes individual devices for receiving inputs by the patient 108, generating outputs for the patient 108, or both. Examples of such individual devices include a screen that could be a touch screen, a physical keypad, an optical finger interface, one or more speakers, one or more microphones, one or more accelerometers, and the like. Such devices can be included within the housing 1202, or can be added by a separate plugin, such as a keypad, a keyboard, a display, and a speaker. The outputs for the patient 108 can be HPIs, such as sounds, vibrations, lights, images, and the like. Thus, based on selections or inputs by the patient 108 or user 108 to the survey questions presented on the user interface 116, one or more inputs are received which the variable interface module 112 can store and process for adjusting various parameters of the user interface 116. Therefore, the user interface 116 of the mobile communication device 104 can be personalized based on the responses to the survey 500 provided by the patient 108.

The method 1300 further includes updating one or more settings of a graphical user interface (GUI) of the display based on the one or more user inputs, at block 1306. In embodiments, the one or more settings may include change of language, font size, button size, background color, and the like on the user interface 116 (or GUI) on the display of the mobile communication device 104, as described above in conjunction with FIG. 5. The patient 108 responds to the survey questions as part of the survey 500 presented on the user interface 116 of the mobile communication device 104. Based on the one or more user inputs, the one or more settings of the user interface 116 may be updated. Updating such settings of the user interface 116 may provide better user experience and comfort to the patients or users while using the respective mobile communication device 104. In some embodiments, the one or more settings may be automatically updated to increase communication between the wearable medical device 102, the mobile communication device 104, and the remote server 106 when an interaction threshold is exceeded.

Further, the method 1300 further includes providing one or more patient engagement features on the display to increase patient engagement with the mobile device, at block 1308. In embodiments, the mobile communication device 104 presents one or more patient engagement features on the display via the user interface 116. The one or more patient engagement features include but are not limited to interactive games, notifications, programmable timed messages, photos, music, podcasts, and news stories. In some embodiments, there may be several additional features to encourage patients to use the mobile communication device 104 and/or act as incentives for the patients to keep the mobile communication device 104 consistently paired with the wearable medical device 102. In the embodiments discussed herein, the one or more patient engagement features are configured to increase patient engagement with the mobile communication device 104, thereby increasing a duration of established communication between the mobile communication device 104, the wearable medical device 102, and the remote server 106.

It will be apparent to a person skilled in the art that the patient engagement feature(s) may be provided on the display after pairing the mobile communication device 104 with the wearable medical device 102, or before pairing (e.g., during power on of the mobile communication device 104) to encourage the patient 108 to pair the aforementioned devices. In certain embodiments, the patient engagement feature(s) may be presented periodically to encourage the patient 108 to keep the mobile communication device 104 consistently paired with the wearable medical device 102. The periodicity, as an example, may be once or twice a day during normal waking hours of the patient 108.

Apart from the patient engagement feature(s) described previously, an engagement feature may include an Avatar (or virtual assistant) that may auto launch periodically or appropriately. The Avatar, in certain embodiments, may be provided by the application running on the mobile communication device 104 or may be an add-on feature provided by an external entity on the user interface 116 or the application. Further, the Avatar may be an AI-based virtual assistant that may generate engagement content such as but not limited to jokes, riddles, puzzles, and the like using context-based AI prompts and/or large language models (LLMs). As an example, the Avatar may generate a prompt such as "Dr. ABC wants you to take 5000 steps per day and you have taken only 1264 steps. Let's take a quick walk around the block." The exemplary prompt may be generated by the Avatar based on medical diagnosis by a specific doctor, patient's medical history, undergoing treatment, patient's daily activities, and/or patient's current health condition. Such prompts may be helpful in engaging the patient 108, instilling a personalized feel, and activating a healthy lifestyle for the patient 108, such that patient's current medical condition inches towards improvement.

In certain embodiments, the application may periodically ask if the patient 108 would like to use one or more patient engagement features. Based on the response of the patient 108 via selecting appropriate button or icon on the user interface 116, the application or user interface 116 may present engagement feature(s). Exemplary engagement questions may be presented to the user 108 or patient 108 such as but not limited to "Do you want to hear a joke?", "Do you want to play a game of wordle?", "How are you feeling right now?", riddles like "What belongs to you but is used more by others?", and/or the like. As previously described, the responses of the patient 108 to the one or more survey questions may be used as a cue by the application or Avatar to generate personalized content for engagement feature(s).

Further, the method 1300 further includes establishing communication between the wearable medical device and the mobile device when the mobile device is powered on and in a predetermined range of the wearable medical device, at block 1310. In embodiments, when the mobile communication device 104 is powered on and is located in a predetermined range of the wearable medical device 102, a communication is established between the wearable medical device 102 and the mobile communication device 104. The established communication may be a wireless connection between the wearable medical device 102 and the mobile communication device 104 using a wireless technology such as Bluetooth, Wi-fi, Zigbee, and/or the like.

Further, the method 1300 further includes transmitting patient data from the wearable medical device to one or more remote servers via the mobile device, at block 1312. In embodiments, the communication may be established between the mobile communication device 104 and the remote server 106 using wireless technology such as Wi-fi, Internet, and the like. The patient data storage module 109 (as described above in conjunction with FIG. 1) of the wearable medical device 102 may store the patient data while the wearable medical device 102 is worn by the patient 108. After the communication is established between the wearable medical device 102, the mobile communication device 104, and the remote server 106, the patient data is transmitted from the patient data storage module 109 of the wearable medical device 102 to the remote server 106 through the mobile communication device 104. It will be apparent to a person skilled in the art that communication between the wearable medical device 102 and the mobile communication device 104, and between the mobile communication device 104 and the remote server 106 may be established by different technologies. As an example, the former entities may be connected via Bluetooth, while the latter entities may be connected via Wi-Fi. Other technologies, as described above in conjunction with previous figures, may be utilized for establishing communication between entities, without limitation.

The remote server 106 (or plurality of servers), after receiving the patient data, may analyze the patient data and follow procedures to respond effectively in case of emergencies. For example, the remote server 106 may provide the patient data to a medical service provider for taking quick action in case the analysis of patient data reveals that the patient 108 is experiencing a medical emergency. As another example, the remote server 106 may utilize the location information of the patient 108, included in the patient data, to provide assistance to the patient 108. Subsequently, local emergency services or medical facilities that are in close proximity to the patient's location may be identified to provide medical care required by the patient 108. As yet another example, medical history of the patient 108 along with the patient vitals included in the patient data may allow the remote server 106 to decide a course of remedial action for the patient 108. The remedial action may include contacting a physician of the patient 108, contacting a family member of the patient 108, contacting a third party for assistance, and the like.

Various embodiments disclosed throughout the present disclosure provide several advantages. Customization of user interfaces to optimize patients' mobile communication devices in accordance with their level of comfort with technology enhances patient engagement with the medical systems and increases the likelihood of patients wearing the respective wearable medical devices (e.g., WCD) for the recommended amount of time per day. Further, consistent patient pairing with mobile communication devices improves the ability of the mobile communication devices and remote server(s) to work quickly and efficiently in case of cardiac events. Furthermore, real time patient data transmission to the remote server(s) enables verification of patient usage of the wearable medical devices or medical system.

Other embodiments include combinations and sub-combinations of features described or shown in the drawings herein, including for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

These and other changes can be made to the embodiments in light of the above-detailed description. In general, in the following claims, the terms used should not be construed to limit the claims to the specific embodiments disclosed in the specification and the claims but should be construed to include all possible embodiments along with the full scope of equivalents to which such claims are entitled. Accordingly, the claims are not limited by the disclosure.

What is claimed is:

1. A medical system comprising:
a wearable medical device comprising a patient data storage module operable to store patient data, the wearable medical device configured to be worn by a patient, wherein the wearable medical device is configured to provide therapy to the patient upon detection of a cardiac condition of the patient based on the patient data;
one or more remote servers; and
a mobile device comprising at least one processor and a display, the mobile device configured to establish communication between the wearable medical device and the one or more remote servers, the at least one processor configured to:
establish communication between the mobile device, the wearable medical device, and the one or more remote servers when the mobile device is powered on and within a predetermined range of the wearable medical device;
provide an interactive survey on the display to receive one or more user inputs;
update a graphical user interface on the display based on the one or more user inputs; and
cause one or more patient engagement features to be displayed on the display, the one or more patient engagement features configured to increase patient engagement with the mobile device, thereby increasing a duration of established communication between the mobile device, the wearable medical device, and the one or more remote servers,
wherein when communication is established between the mobile device, the wearable medical device, and the one or more remote servers, patient data is transmitted to the one or more remote servers from the patient data storage module.

2. The medical system of claim 1, wherein the interactive survey comprises one or more visual interface selections including one or more of a language selection, a mobile device usage level selection, a level of instruction detail selection, a button size selection, a font size selection, and a background color selection.

3. The medical system of claim 2, wherein the interactive survey further comprises one or more audio interface selections.

4. The medical system of claim 1, wherein the one or more patient engagement features include interactive games, notifications, programmable timed messages, photos, music, podcasts, and news stories.

5. The medical system of claim 1, wherein the one or more patient engagement features include provision of a heart award to the patient based on a total time for which the wearable medical device is being worn by the patient.

6. The medical system of claim 1, wherein the at least one processor is further configured to automatically update one or more settings to increase communication between the wearable medical device, the mobile device, and the one or more remote servers when an interaction threshold is exceeded.

7. The medical system of claim 1, wherein the one or more remote servers are configured to analyze patient data and provide patient data to medical service providers.

8. The medical system of claim 1, wherein the one or more remote servers are configured to alert first responders of a medical emergency when patient data from the wearable medical device indicates that the patient is experiencing the medical emergency.

9. The medical system of claim 1, wherein the wearable medical device further comprises a connection verification module which is configured to provide an alert when the wearable medical device is being worn by the patient and communication has not been established between the wearable medical device, the mobile device, and the one or more remote servers for a disconnection duration, and wherein the alert is an audible alert or visual alert provided on the wearable medical device.

10. The medical system of claim 1, wherein when communication between the mobile device, the wearable medical device, and the one or more remote servers is not established, no patient data is transmitted from the wearable medical device to the one or more remote servers.

11. A method for transmitting patient data between a wearable medical device worn by a patient and one or more remote servers, the method comprising:
providing an interactive survey on a display of a mobile device;
receiving one or more user inputs in response to the interactive survey;
updating one or more settings of a graphical user interface of the display based on the one or more user inputs;
providing one or more patient engagement features on the display to increase patient engagement with the mobile device;
establishing communication between the wearable medical device and the mobile device when the mobile device is powered on and in a predetermined range of the wearable medical device; and transmitting patient data from the wearable medical device to the one or more remote servers via the mobile device, wherein the one or more patient engagement features increase a communication duration of established communication between the wearable medical device, the mobile device, and the one or more remote servers.

12. The method of claim 11, wherein the interactive survey comprises one or more audio interface selections and/or one or more visual interface selections including one or more of a language selection, a mobile device usage level selection, a level of instruction detail selection, a button size selection, a font size selection, and a background color selection.

13. The method of claim 11, wherein the one or more patient engagement features include interactive games, notifications, programmable timed messages, photos, music, podcasts, and news stories.

14. The method of claim 11, wherein providing the one or more patient engagement features on the display comprises providing a heart award to the patient based on a total time for which the wearable medical device is being worn by the patient.

15. The method of claim 11, wherein the one or more remote servers are configured to analyze patient data and provide patient data to medical service providers.

16. The method of claim 11, the method further comprising transmitting an alert to first responders when patient data from the wearable medical device indicates a patient is experiencing a medical emergency.

17. The method of claim 11, the method further comprising providing an alert, via a connection verification module of the wearable medical device, when the wearable medical device is being worn by a patient and communication has not been established between the wearable medical device, the mobile device, and the one or more remote servers for a disconnection duration, wherein the alert is an audible or visual alert provided by the wearable medical device.

18. A non-transitory computer readable medium, encoded with instructions for increasing patient engagement with a mobile device and transmitting patient data between a wearable medical device and one or more remote servers via the mobile device stored thereon, that when executed by at least one computing device causes the at least one computing device to perform operations for increasing patient engagement and transmission of patient data, the operations comprising:

providing an interactive survey on a display of the mobile device;

receiving one or more user inputs in response to the interactive survey;

updating one or more settings of a graphical user interface of the display based on the one or more user inputs;

providing one or more patient engagement features on the display to increase patient engagement with the mobile device;

establishing communication between the wearable medical device and the mobile device when the mobile device is powered on and in a predetermined range of the wearable medical device; and transmitting patient data from the wearable medical device to the one or more remote servers via the mobile device, wherein the one or more patient engagement features increase a communication duration of established communication between the wearable medical device, the mobile device, and the one or more remote servers.

19. The non-transitory computer readable medium of claim 18, wherein the interactive survey comprises one or more audio interface selections and/or one or more visual interface selections including one or more of a language selection, a mobile device usage level selection, a level of instruction detail selection, a button size selection, a font size selection, and a background color selection.

20. The non-transitory computer readable medium of claim 18, wherein providing the one or more patient engagement features on the display comprises providing a heart award and a compliance status tier based on a total time for which the wearable medical device is being worn by a patient.

\* \* \* \* \*